United States Patent
Dransfield et al.

(10) Patent No.: US 12,371,414 B2
(45) Date of Patent: *Jul. 29, 2025

(54) METHODS OF TREATING NEUROLOGICAL DISORDERS

(71) Applicant: NEUMORA THERAPEUTICS, INC., Watertown, MA (US)

(72) Inventors: Paul Dransfield, Arlington, MA (US); Dilinie Fernando, Jamaica Plain, MA (US); James Harvey, Arlington, MA (US); Brian Sparling, Saugus, MA (US); John Stellwagen, Newbury Park, CA (US); Zhihua Ma, Lexington, MA (US); Anne-Marie Beausoleil, Redwood City, CA (US); Ryan Hudson, Weston, MA (US)

(73) Assignee: Neumora Therapeutics, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/628,594

(22) Filed: Apr. 5, 2024

(65) Prior Publication Data

US 2024/0294492 A1 Sep. 5, 2024

Related U.S. Application Data

(63) Continuation of application No. 18/526,960, filed on Dec. 1, 2023, now Pat. No. 11,993,580.

(60) Provisional application No. 63/429,760, filed on Dec. 2, 2022.

(51) Int. Cl.
C07D 401/04 (2006.01)

(52) U.S. Cl.
CPC .................. C07D 401/04 (2013.01)

(58) Field of Classification Search
CPC .................................................. C07D 401/04
See application file for complete search history.

(56) References Cited

U.S. PATENT DOCUMENTS

| | | | |
|---|---|---|---|
| 6,096,753 | A | 8/2000 | Spohr et al. |
| 6,649,604 | B2 | 11/2003 | Spohr et al. |
| 7,582,631 | B2 | 9/2009 | Dominguez et al. |
| 11,993,590 | B2 | 5/2024 | Dransfield et al. |
| 2005/0020646 | A1 | 1/2005 | Newgreen et al. |
| 2005/0043301 | A1 | 2/2005 | Liu et al. |
| 2005/0084808 | A1 | 4/2005 | Kong et al. |
| 2010/0039026 | A1 | 2/2010 | Yang et al. |
| 2013/0158031 | A1 | 6/2013 | Cai et al. |
| 2019/0054074 | A1 | 2/2019 | Wada et al. |
| 2021/0119138 | A1 | 4/2021 | Yamatani et al. |
| 2024/0246928 | A1 | 7/2024 | Dransfield et al. |

FOREIGN PATENT DOCUMENTS

| | | |
|---|---|---|
| AR | 098136 | 5/2016 |
| CN | 102875479 | 1/2013 |
| CN | 106928204 | 7/2017 |
| CN | 110964037 | 4/2020 |
| CN | 112375088 | 2/2021 |
| CN | 112480113 | 3/2021 |
| DE | 1271116 | 6/1968 |
| DE | 10238725 | 3/2004 |
| EP | 0391254 | 10/1990 |
| EP | 0542372 | 5/1993 |
| EP | 2543372 | 1/2013 |
| EP | 3015527 | 4/2018 |
| JP | 2006028056 | 2/2006 |
| JP | 2007145819 | 6/2007 |
| JP | 2007176933 | 7/2007 |
| JP | 2011088888 | 5/2011 |
| KR | 20210088789 | 7/2021 |
| KR | 20220020447 | 2/2022 |
| WO | WO 1998024780 | 6/1998 |
| WO | WO 1998024782 | 6/1998 |
| WO | WO 1998028299 | 7/1998 |
| WO | WO 1999028303 | 6/1999 |
| WO | WO 2001000562 | 1/2001 |
| WO | WO 2001019814 | 3/2001 |
| WO | WO 2002015902 | 2/2002 |

(Continued)

OTHER PUBLICATIONS

Joshi, BMC Bioinformatics, 2016, vol. 17(Suppl 19):515, 283-295. (Year: 2016).*
Cuevas, Neurobiology of Disease, vol. 192, (2024), 106430, 1-16. (Year: 2024).*
Salado, J Med Chem, 2014, 57, 2755-2772. (Year: 2014).*
Chen et al., "A Novel Biotransformation of Alkyl Aminopyrrolidine to Aminopiperidine Ring by Human CYP3A," Drug Metabolism and Disposition, Sep. 2011, 39(9): 1668-1673 (abstract only).
Kabbe, "Heterocyclen aus Carbonsäurederivaten, II. Substituierte 4-Hydroxy- und 4-Amino-pyrimidine," Chemistry Europe, Jun. 1967, 704(1): 144-149 (abstract only).

(Continued)

*Primary Examiner* — D Margaret M Seaman
(74) *Attorney, Agent, or Firm* — Fish & Richardson P.C.

(57) ABSTRACT

The present disclosure relates to compounds of Formula (I),

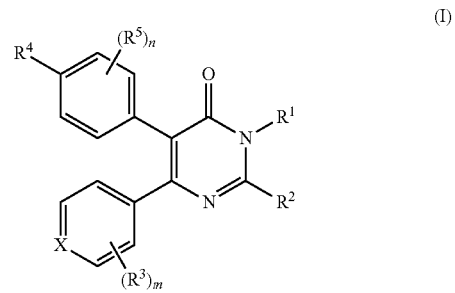

and pharmaceutically acceptable salts thereof, wherein the variable are as described herein, and compositions and uses of same for treating neurological disorders.

6 Claims, No Drawings

Specification includes a Sequence Listing.

(56) References Cited

FOREIGN PATENT DOCUMENTS

| | | |
|---|---|---|
| WO | WO 2002072145 | 9/2002 |
| WO | WO 2002076438 | 10/2002 |
| WO | WO 2003044021 | 5/2003 |
| WO | WO 2003077656 | 9/2003 |
| WO | WO 2003084935 | 10/2003 |
| WO | WO 2003099808 | 12/2003 |
| WO | WO 2004005283 | 1/2004 |
| WO | WO 2004029204 | 4/2004 |
| WO | WO 2004092120 | 10/2004 |
| WO | WO 2004092121 | 10/2004 |
| WO | WO 2004113419 | 12/2004 |
| WO | WO 2005026148 | 3/2005 |
| WO | WO 2005070934 | 8/2005 |
| WO | WO 2005105790 | 11/2005 |
| WO | WO 2005115984 | 12/2005 |
| WO | WO 2006051311 | 5/2006 |
| WO | WO 2006058535 | 6/2006 |
| WO | WO 2006066070 | 6/2006 |
| WO | WO 2007009120 | 1/2007 |
| WO | WO 2008130481 | 10/2008 |
| WO | WO 2009050523 | 4/2009 |
| WO | WO 2009095773 | 8/2009 |
| WO | WO 2009108657 | 9/2009 |
| WO | WO 2009119537 | 10/2009 |
| WO | WO 2009158473 | 12/2009 |
| WO | WO 2010081851 | 7/2010 |
| WO | WO 2010139982 | 12/2010 |
| WO | WO 2011076419 | 6/2011 |
| WO | WO 2011143495 | 11/2011 |
| WO | WO 2012004217 | 1/2012 |
| WO | WO 2012068335 | 5/2012 |
| WO | WO 2013007708 | 1/2013 |
| WO | WO 2013007792 | 1/2013 |
| WO | WO 2013033240 | 3/2013 |
| WO | WO 2013096093 | 6/2013 |
| WO | WO 2013139822 | 9/2013 |
| WO | WO 2013167633 | 11/2013 |
| WO | WO 2014059232 | 4/2014 |
| WO | WO 2015037680 | 3/2015 |
| WO | WO 2015061247 | 4/2015 |
| WO | WO 2015069752 | 5/2015 |
| WO | WO 2015168466 | 11/2015 |
| WO | WO 2015191382 | 12/2015 |
| WO | WO 2016024745 | 2/2016 |
| WO | WO 2016042341 | 3/2016 |
| WO | WO 2016101119 | 6/2016 |
| WO | WO 2016106106 | 6/2016 |
| WO | WO 2018013772 | 1/2018 |
| WO | WO 2018031658 | 2/2018 |
| WO | WO 2018119374 | 6/2018 |
| WO | WO 2018127801 | 7/2018 |
| WO | WO 2019173653 | 9/2019 |
| WO | WO 2020161162 | 8/2020 |
| WO | WO 2020198710 | 10/2020 |
| WO | WO 2020210404 | 10/2020 |
| WO | WO 2020257653 | 12/2020 |
| WO | WO 2021026047 | 2/2021 |
| WO | WO 2021194914 | 9/2021 |
| WO | WO 2021225912 | 11/2021 |
| WO | WO 2022076627 | 4/2022 |

OTHER PUBLICATIONS

Laufer et al., "From Imidazoles to Pyrimidines: New Inhibitors of Cytokine Release," J. Med. Chem., 2002, 2733-2740.

Lu et al., "An efficient one-pot construction of substituted pyrimidinones," Tetrahedron, 2006, 62:11714-11723.

Ross et al., "High-Content Screening Analysis of the p38 Pathway: Profiling of Structurally Related p38α Kinase Inhibitors Using Cell-Based Assays," Assay and Drug Development Technologies, Aug. 31, 2006, 4(4): 2 pages (abstract only).

Zhang et al., "Carbon-carbon bond construction at the 2-position of polysubstituted pyrimidinones," Tetrahedron Letters, Aug. 2002, 43:8901-8903.

* cited by examiner

SEQUENCE LISTING

```
Sequence total quantity: 2
SEQ ID NO: 1          moltype = AA  length = 415
FEATURE               Location/Qualifiers
source                1..415
                      mol_type = protein
                      organism = Homo sapiens
SEQUENCE: 1
MELRVGNRYR LGRKIGSGSF GDIYLGTDIA AGEEVAIKLE CVKTKHPQLH IESKIYKMMQ    60
GGVGIPTIRW CGAEGDYNVM VMELLGPSLE DLFNFCSRKF SLKTVLLLAD QMISRIEYIH   120
SKNFIHRDVK PDNFLMGLGK KGNLVYIIDF GLAKKYRDAR THQHIPYREN KNLTGTARYA   180
```

```
SINTHLGIEQ  SRRDDLESLG  YVLMYFNLGS  LPWQGLKAAT  KRQKYERISE  KKMSTPIEVL   240
CKGYPSEFAT  YLNFCRSLRF  DDKPDYSYLR  QLFRNLFHRQ  GFSYDYVFDW  NMLKFGASRA   300
ADDAERERRD  REERLRHSRN  PATRGLPSTA  SGRLRGTQEV  APPTPLTPTS  HTANTSPRPV   360
SGMERERKVS  MRLHRGAPVN  ISSSDLTGRQ  DTSRMSTSQI  PGRVASSGLQ  SVVHR        415

SEQ ID NO: 2            moltype = AA  length = 414
FEATURE                 Location/Qualifiers
source                  1..414
                        mol_type = protein
                        organism = Homo sapiens
SEQUENCE: 2
MSEYIRVTED  ENDEPIEIPS  EDDGTVLLST  VTAQFPGACG  LRYRNPVSQC  MRGVRLVEGI    60
LHAPDAGWGN  LVYVVNYPKD  NKRKMDETDA  SSAVKVKRAV  QKTSDLIVLG  LPWKTTEQDL   120
KEYFSTFGEV  LMVQVKKDLK  TGHSKGFGFV  RFTEYETQVK  VMSQRHMIDG  RWCDCKLPNS   180
KQSQDEPLRS  RKVFVGRCTE  DMTEDELREF  FSQYGDVMDV  FIPKPFRAFA  FVTFADDQIA   240
QSLCGEDLII  KGISVHISNA  EPKHNSNRQL  ERSGRFGGNP  GGFGNQGGFG  NSRGGGAGLG   300
NNQGSNMGGG  MNFGAFSINP  AMMAAAQAAL  QSSWGMMGML  ASQQNQSGPS  GNNQNQGNMQ   360
REPNQAFGSG  NNSYSGSNSG  AAIGWGSASN  AGSGSGFNGG  FGSSMDSKSS  GWGM         414
```

METHODS OF TREATING NEUROLOGICAL DISORDERS

CROSS-REFERENCE TO RELATED APPLICATIONS

This application is a continuation of U.S. patent application Ser. No. 18/526,960, filed on Dec. 1, 2023, which claims priority to U.S. Provisional Application No. 63/429,760, filed on Dec. 2, 2022. The disclosure of the prior applications is considered part of and is are incorporated by reference in the disclosure of this application.

TECHNICAL FIELD

The present disclosure relates to compounds of Formula (I), and pharmaceutically acceptable salts thereof, and compositions and uses of same for treating neurological disorders.

SEQUENCE LISTING

This application contains a Sequence Listing that has been submitted electronically as an XML file named "52308-0020001.XML." The XML file, created on Nov. 20, 2023, is 3,556 bytes in size. The material in the XML file is hereby incorporated by reference in its entirety.

BACKGROUND

Proteinopathies are a class of disorders where a protein or proteins become misfolded and/or structurally abnormal, typically resulting in a loss of function and/or gain of a toxic, pathological function. Proteinopathies can be caused by, for example, aberrant post-translational modification such as hyperphosphorylation, truncation, or expansion of the polypeptide sequence due to mutation of the encoding gene sequence, or leading to mislocalization and aggregation of the protein within the cell.

Casein kinase 1 delta (CK-1δ or CK-1d) is a member of the casein kinase 1 (CK1) family of protein kinases, which are serine/threonine-selective kinases that function as regulators of signal transduction pathways in most eukaryotic cell types. Mammals have seven CK1 family members encoded by distinct genes: alpha, beta 1, gamma 1, gamma 2, gamma 3, delta, and epsilon. The CK1 protein kinases range from 22 to 55 kDa and have been identified in the membranes, nucleus, and cytoplasm of eukaryotes and additionally in the mitotic spindle in mammalian cells.

TAR DNA-Binding Protein (TDP-43) is a nuclear DNA/RNA binding protein that plays a role in RNA transcription, maturation, and stability. Mislocalization of TDP-43 can trigger a variety of downstream pathological processes such as sequestration of a hyperphosphorylated, ubiquitinated, and cleaved form of the protein in cytoplasmic aggregates. CK-1δ is one of several protein kinases that can phosphorylate TDP-43. CK-1δ has been implicated in the aberrant hyperphosphorylation of TDP-43 in the cytoplasm, including at serines 409 and 410, sites which are thought to be representative markers of neuropathology.

SUMMARY

Some embodiments provide a compound of Formula (I),

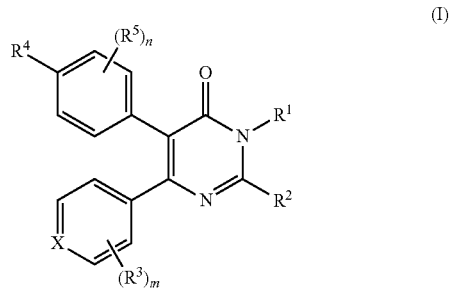

(I)

or a pharmaceutically acceptable salt thereof, wherein:

$R^1$ is hydrogen or C1-C6 alkyl;

$R^2$ is C1-C8 alkyl, C1-C8 haloalkyl, C3-C8 cycloalkyl, or $-NR^A R^B$;

$R^A$ and $R^B$ are independently hydrogen or C1-C6 alkyl, or $R^A$ and $R^B$ together with the nitrogen atom to which they are attached form a 4-6 membered heterocyclyl;

each $R^3$ is independently halogen, cyano, hydroxyl, or C1-C6 alkyl;

X is CH, $CR^3$, or N;

$R^4$ is chloro, cyano, hydroxyl, or trifluoromethyl;

each $R^5$ is independently halogen, cyano, hydroxyl, C1-C6 alkyl, or C1-C6 haloalkyl; and m and n are independently 0, 1, 2, or 3.

Some embodiments provide a compound selected from the group consisting of:

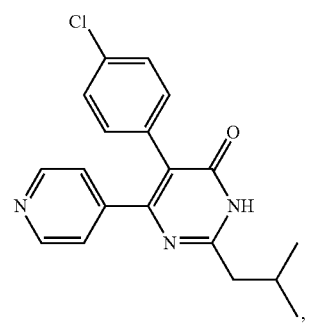

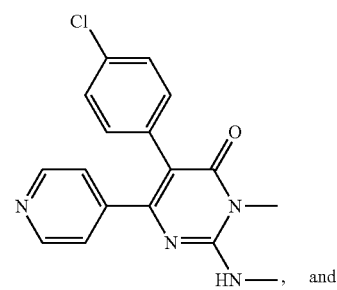

and

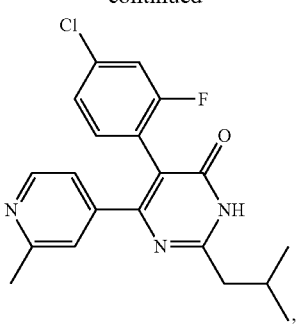

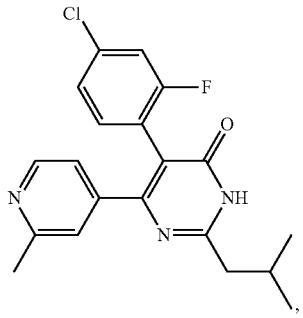

or a pharmaceutically acceptable salt of any of the foregoing.

Some embodiments provide a compound which is 5-(4-chlorophenyl)-2-isobutyl-6-(pyridin-4-yl)pyrimidin-4(3H)-one, or a pharmaceutically acceptable salt thereof, having the structure of

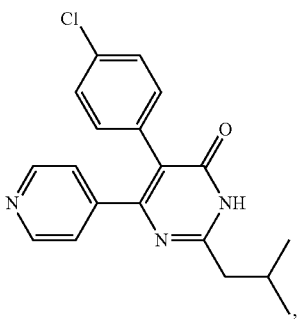 [SMILES: CC(C)Cc1nc(-c2ccncc2)c(-c2ccc(Cl)cc2)c(=O)[nH]1]

or a pharmaceutically acceptable salt thereof.

Some embodiments provide a compound which is 5-(4-chlorophenyl)-3-methyl-2-(methylamino)-6-(pyridin-4-yl)pyrimidin-4(3H)-one, or a pharmaceutically acceptable salt thereof, having the structure of

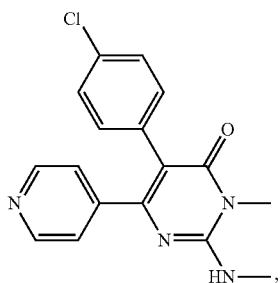 [SMILES: CNc1nc(-c2ccncc2)c(-c2ccc(Cl)cc2)c(=O)n1C]

or a pharmaceutically acceptable salt thereof.

Some embodiments provide a compound which is 5-(4-chloro-2-fluorophenyl)-2-isobutyl-6-(2-methylpyridin-4-yl)pyrimidin-4(3H)-one, or a pharmaceutically acceptable salt thereof, having the structure of or a pharmaceutically acceptable salt thereof.

Some embodiments provide a pharmaceutical composition comprising a compound of Formula (I), or a pharmaceutically acceptable salt thereof, and one or more pharmaceutically acceptable excipients.

Some embodiments provide a method of treating a CK-1δ-associated neurological disorder in a subject in need thereof, comprising administering to the subject a therapeutically effective amount of a compound of Formula (I), or a pharmaceutically acceptable salt thereof, or a pharmaceutical composition comprising a compound of Formula (I), or a pharmaceutically acceptable salt thereof, and one or more pharmaceutically acceptable excipients.

Some embodiments provide a method of inhibiting TDP-43 phosphorylation in a cell comprising TDP-43 and CK-1δ, the method comprising contacting the cell with a compound of Formula (I), or a pharmaceutically acceptable salt thereof.

DETAILED DESCRIPTION

Casein Kinase 1 Delta

CK-1δ is encoded by the CSNK1D gene located at chromosome 17q25.3 (chr17:82,239,019-82,273,750, GRCh38/hg38). The CSNK1D mRNA polynucleotide sequence encoding CK-1δ is NCBI Reference Sequence: NM_001893.6.

The CSNK1D mRNA polynucleotide sequence encoding CK-1δ can be alternatively spliced, for example CSNK1D transcript variant 2 has been reported (NCBI Reference Sequence: NM_139062.4), and CSNK1D transcript variant 4 has been reported (NCBI Reference Sequence: NM_001363749.2).

The 415 amino acid polypeptide sequence of the CK-1δ protein (UniProt P48730) is listed below as SEQ ID NO: 1:

MELRVGNRYRLGRKIGSGSFGDIYLGTDIAAGEEVAIKLECVKTKHPQLH

IESKIYKMMQGGVGIPTIRWCGAEGDYNVMVMELLGPSLEDLFNFCSRKF

SLKTVLLLADQMISRIEYIHSKNFIHRDVKPDNFLMGLGKKGNLVYIIDF

GLAKKYRDARTHQHIPYRENKNLTGTARYASINTHLGIEQSRRDDLESLG

YVLMYFNLGSLPWQGLKAATKRQKYERISEKKMSTPIEVLCKGYPSEFAT

YLNFCRSLRFDDKPDYSYLRQLFRNLFHRQGFSYDYVFDWNMLKFGASRA

ADDAERERRDREEERLRHSRNPATRGLPSTASGRLRGTQEVAPPTPLTPTS

HTANTSPRPVSGMERERKVSMRLHRGAPVNISSSDLTGRQDTSRMSTSQI

PGRVASSGLQSVVHR

TAR DNA-Binding Protein

TDP-43 is encoded by the TARDBP gene located at chromosome 1p36.22 (chr1:11,012,654-11,030,528, GRCh38/hg38). The TARDBP mRNA polynucleotide sequence encoding TDP-43 is NCBI Reference Sequence: NM_007375.4.

The 414 amino acid polypeptide sequence of the TDP-43 protein (UniProt Q13148) is listed below as SEQ ID NO: 2:

MSEYIRVTEDENDEPIEIPSEDDGTVLLSTVTAQFPGACGLRYRNPVSQC

MRGVRLVEGILHAPDAGWGNLVYVVNYPKDNKRKMDETDASSAVKVKRAV

QKTSDLIVLGLPWKTTEQDLKEYFSTFGEVLMVQVKKDLKTGHSKGFGFV

RFTEYETQVKVMSQRHMIDGRWCDCKLPNSKQSQDEPLRSRKVFVGRCTE

DMTEDELREFFSQYGDVMDVFIPKPFRAFAFVTFADDQIAQSLCGEDLII

KGISVHISNAEPKHNSNRQLERSGRFGGNPGGFGNQGGFGNSRGGGAGLG

NNQGSNMGGGMNFGAFSINPAMMAAAQAALQSSWGMMGMLASQQNQSGPS

GNNQNQGNMQREPNQAFGSGNNSYSGSNSGAAIGWGSASNAGSGSGENGG

FGSSMDSKSSGWGM

Mutations of the TARDBP gene encoding the TDP-43 protein have been associated with various neurological disorders including, for example, amyotrophic lateral sclerosis (ALS) and frontotemporal dementia (FTD). Mutations of TARDBP associated with ALS and FTD are described, for example, in Table 1 below.

TABLE 1

OMIM Allelic Variants - 605078

| Number | Phenotype | Mutation | SNP |
|---|---|---|---|
| .0001 | ALS | MET337VAL | rs80356730 |
| .0002 | ALS | GLN331LYS | rs80356727 |
| .0003 | ALS | GLY294ALA | rs80356721 |
| .0004 | ALS | GLY290ALA | rs121908395 |
| .0005 | ALS | GLY298SER | rs4884357 |
| .0006 | ALS | ASP169GLY | rs80356717 |
| .0007 | ALS | GLY348CYS | rs80356733 |
| .0008 | ALS | GLN343ARG | rs80356731 |
| .0009 | ALS | ALA315THR | rs80356726 |
| .0010 | ALS | GLY295SER | rs80356723 |
| .0011 | FTD | LYS263GLU | rs267607102 |
| .0012 | ALS and FTD | 2076G-A, 3-PRIME UTR | rs387906334 |
| .0013 | ALS and FTD | ALA382THR | rs367543041 |

Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

The term "about" when referring to a number or a numerical range means that the number or numerical range referred to is an approximation, for example, within experimental variability and/or statistical experimental error, and thus the number or numerical range may vary up to ±10% of the stated number or numerical range.

The term "acceptable" with respect to a formulation, composition or ingredient, as used herein, means having no persistent detrimental effect on the general health of the subject being treated.

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described herein form with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

As used herein, the "subject" refers to any animal, including mammals such as primates (e.g., humans), mice, rats, other rodents, rabbits, dogs, cats, swine, cattle, sheep, horses, primates, and humans. In some embodiments, the subject is a human. In some embodiments, the subject has experienced and/or exhibited at least one symptom of the disorder to be treated.

"Treatment" or "therapy" of a subject refers to any type of intervention or process performed on, or the administration of an active agent to, the subject with the objective of reversing, alleviating, ameliorating, inhibiting, slowing down, or preventing the onset, progression, development, severity, or recurrence of a symptom, complication, condition, or biochemical indicia associated with a disease. In some embodiments, the disease is a neurological disorder. As used herein, the terms "treatment" and "treating" when referring, e.g., to the treatment of a neurological disorder, are not intended to be absolute terms. For example, "treatment of a neurological disorder" and "treating a neurological disorder", as used in a clinical setting, is intended to include obtaining beneficial or desired clinical results and can include an improvement in the condition of a subject having a neurological disorder. Beneficial or desired clinical results include, but are not limited to, one or more of the following:

reducing the rate of disease progression, reducing severity and/or frequency of symptoms, reducing biochemical and/or cellular indicia of a particular disease or disorder, an increase in the period of remission (partial or complete) for a subject (e.g., as compared to the one or more metric(s) in a subject having a similar disorder receiving no treatment or a different treatment, or as compared to the one or more metric(s) in the same subject prior to treatment), increasing the quality of life of those suffering from a disease (e.g., assessed using a clinical questionnaire), and/or prolonging survival of subjects having a disease. "Treatment" can also mean prolonging survival as compared to expected survival if not receiving treatment.

The phrase "therapeutically effective amount" means an amount of compound that, when administered to a subject in need of such treatment, is sufficient to (i) treat a CK-1δ-associated disease or disorder, (ii) attenuate, ameliorate, or eliminate one or more symptoms of the particular disease, condition, or disorder, or (iii) delay the onset of one or more symptoms of the particular disease, condition, or disorder described herein.

The term "inhibit" or "inhibition of" means to reduce by a measurable amount, or to prevent entirely (e.g., 100% inhibition).

The term "halo" or "halogen" refers to fluoro (F), chloro (Cl), bromo (Br), or iodo (I).

The term "cyano" refers to a —CN radical.

The term "hydroxyl" refers to an —OH radical.

The term "alkyl" refers to a saturated acyclic hydrocarbon radical that may be a straight chain or branched chain, containing the indicated number of carbon atoms. For example, C1-C10 indicates that the group may have from 1 to 10 (inclusive) carbon atoms in it. Non-limiting examples include methyl, ethyl, iso-propyl, tert-butyl, n-hexyl. The term "saturated" as used in this context means only single bonds present between constituent carbon atoms and other available valences occupied by hydrogen and/or other substituents as defined herein.

The term "haloalkyl" refers to an alkyl, in which one or more hydrogen atoms is/are replaced with an independently selected halogen atom.

The term "cycloalkyl" as used herein refers to cyclic saturated or partially unsaturated hydrocarbon groups having, e.g., 3 to 20 ring carbons, preferably 3 to 16 ring carbons, and more preferably 3 to 12 ring carbons or 3-10 ring carbons or 3-6 ring carbons, wherein the cycloalkyl group may be optionally substituted. Examples of cycloalkyl groups include, without limitation, cyclopropyl, cyclobutyl, cyclopentyl, cyclohexyl, cycloheptyl, and cyclooctyl. Cycloalkyl may include multiple fused and/or bridged rings. Non-limiting examples of fused/bridged cycloalkyl includes: bicyclo[1.1.0]butane, bicyclo[2.1.0]pentane, bicyclo[1.1.1]pentane, bicyclo[3.1.0]hexane, bicyclo[2.1.1]hexane, bicyclo[3.2.0]heptane, bicyclo[4.1.0]heptane, bicyclo[2.2.1]heptane, bicyclo[3.1.1]heptane, bicyclo[4.2.0]octane, bicyclo[3.2.1]octane, bicyclo[2.2.2]octane, and the like. Cycloalkyl also includes spirocyclic rings (e.g., spirocyclic bicycle wherein two rings are connected through just one atom). Non-limiting examples of spirocyclic cycloalkyls include spiro[2.2]pentane, spiro[2.5]octane, spiro[3.5]nonane, spiro[3.5]nonane, spiro[3.5]nonane, spiro[4.4]nonane, spiro[2.6]nonane, spiro[4.5]decane, spiro[3.6]decane, spiro[5.5]undecane, and the like. The term "saturated" as used in this context means only single bonds present between constituent carbon atoms.

The term "heterocyclyl" refers to a mono-, bi-, tri-, or polycyclic saturated or partially unsaturated ring system with 3-16 ring atoms (e.g., 5-8 membered monocyclic, 8-12 membered bicyclic, or 11-14 membered tricyclic ring system) having 1-3 heteroatoms if monocyclic, 1-6 heteroatoms if bicyclic, or 1-9 heteroatoms if tricyclic or polycyclic, said heteroatoms selected from O, N, or S (e.g., carbon atoms and 1-3, 1-6, or 1-9 heteroatoms of N, O, or S if monocyclic, bicyclic, or tricyclic, respectively), wherein one or more ring atoms may be substituted by 1-3 oxo (forming, e.g., a lactam) and one or more N or S atoms may be substituted by 1-2 oxido (forming, e.g., an N-oxide, an S-oxide, or an S,S-dioxide), valence permitting; and wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, tetrahydropyridyl, dihydropyrazinyl, dihydropyridyl, dihydropyrrolyl, dihydrofuranyl, dihydrothiophenyl, and the like. Heterocyclyl may include multiple fused and bridged rings. Non-limiting examples of fused/bridged heterocyclyl includes: 2-azabicyclo[1.1.0]butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, 2-azabicyclo[2.2.2]octane, 3-azabicyclo[3.2.1]octane, 2-oxabicyclo[1.1.0]butane, 2-oxabicyclo[2.1.0]pentane, 2-oxabicyclo[1.1.1]pentane, 3-oxabicyclo[3.1.0]hexane, 5-oxabicyclo[2.1.1]hexane, 3-oxabicyclo[3.2.0]heptane, 3-oxabicyclo[4.1.0]heptane, 7-oxabicyclo[2.2.1]heptane, 6-oxabicyclo[3.1.1]heptane, 7-oxabicyclo[4.2.0]octane, 2-oxabicyclo[2.2.2]octane, 3-oxabicyclo[3.2.1]octane, and the like. Heterocyclyl also includes spirocyclic rings (e.g., spirocyclic bicycle wherein two rings are connected through just one atom). Non-limiting examples of spirocyclic heterocyclyls include 2-azaspiro[2.2]pentane, 4-azaspiro[2.5]octane, 1-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[4.5]decane, 7-azaspiro[4.5]decane 2,5-diazaspiro[3.6]decane, 3-azaspiro[5.5]undecane, 2-oxaspiro[2.2]pentane, 4-oxaspiro[2.5]octane, 1-oxaspiro[3.5]nonane, 2-oxaspiro[3.5]nonane, 7-oxaspiro[3.5]nonane, 2-oxaspiro[4.4]nonane, 6-oxaspiro[2.6]nonane, 1,7-dioxaspiro[4.5]decane, 2,5-dioxaspiro[3.6]decane, 1-oxaspiro[5.5]undecane, 3-oxaspiro[5.5]undecane, 3-oxa-9-azaspiro[5.5]undecane and the like.

As used herein, when a ring is described as being "partially unsaturated", it means said ring has one or more additional degrees of unsaturation (in addition to the degree of unsaturation attributed to the ring itself; e.g., one or more double or triple bonds between constituent ring atoms), provided that the ring is not aromatic. Examples of such rings include: cyclopentene, cyclohexene, cycloheptene, and the like.

For the avoidance of doubt, and unless otherwise specified, for rings and cyclic groups (e.g., heterocyclyl, cycloalkyl, and the like described herein) containing a sufficient number of ring atoms to form bicyclic or higher order ring systems (e.g., tricyclic, polycyclic ring systems), it is understood that such rings and cyclic groups encompass those having fused rings, including those in which the points of fusion are located (i) on adjacent ring atoms (e.g., [x.x.0] ring systems, in which 0 represents a zero atom bridge (e.g., 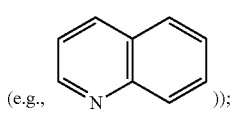 ));

(ii) a single ring atom (spiro-fused ring systems)

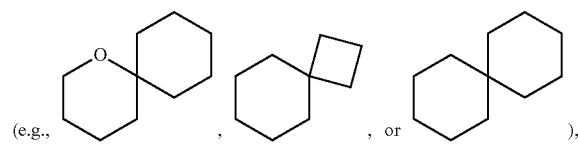

(e.g., , , or ), or (iii) a contiguous array of ring atoms (bridged ring systems having all bridge lengths>0)

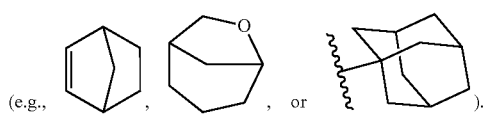

(e.g., , , or ).

In addition, the compounds generically or specifically disclosed herein are intended to include all tautomeric forms. Thus, by way of example, a compound containing the moiety:

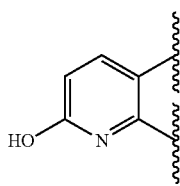 [SMILES: *c1ccc(O)nc1*]

encompasses the tautomeric form containing the moiety:

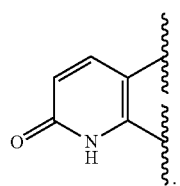

Similarly, a pyridinyl or pyrimidinyl moiety that is described to be optionally substituted with hydroxyl encompasses pyridone or pyrimidone tautomeric forms. For example, it is understood that depictions of Formula (I):

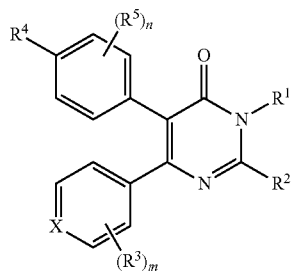

include

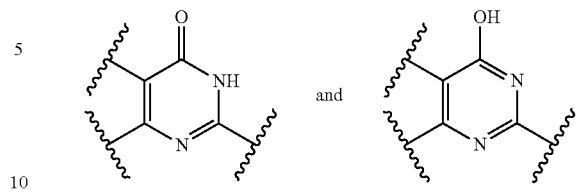

when $R^1$ is hydrogen.

The compounds provided herein may encompass various stereochemical forms. The compounds also encompass enantiomers (e.g., R and S isomers), diastereomers, as well as mixtures of enantiomers (e.g., R and S isomers) including racemic mixtures and mixtures of diastereomers, as well as individual enantiomers and diastereomers, which arise as a consequence of structural asymmetry in certain compounds. Unless otherwise indicated, when a disclosed compound is named or depicted by a structure without specifying the stereochemistry (e.g., a "flat" structure) and has one or more chiral centers, it is understood to represent all possible stereoisomers of the compound. Likewise, unless otherwise indicated, when a disclosed compound is named or depicted by a structure that specifies the stereochemistry (e.g., a structure with "wedge" and/or "dashed" bonds) and has one or more chiral centers, it is understood to represent the indicated stereoisomer of the compound.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, isotopes of carbon include $^{11}C$, $^{13}C$, and $^{14}C$, and isotopes of fluorine include $^{18}F$.

The details of one or more embodiments of this disclosure are set forth in the accompanying drawings and the description below. Other features and advantages of the present disclosure will be apparent from the description and drawings, and from the claims.

Compounds

Some embodiments provide a compound of Formula (I),

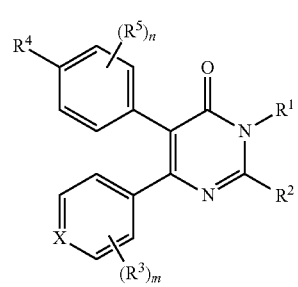

(I)

or a pharmaceutically acceptable salt thereof, wherein:
$R^1$ is hydrogen or C1-C6 alkyl;
$R^2$ is C1-C8 alkyl, C1-C8 haloalkyl, C3-C8 cycloalkyl, or —$NR^A R^B$;
$R^A$ and $R^B$ are independently hydrogen or C1-C6 alkyl, or $R^A$ and $R^B$ together with the nitrogen atom to which they are attached form a 4-6 membered heterocyclyl;

each $R^3$ is independently halogen, cyano, hydroxyl, or C1-C6 alkyl;
X is CH, $CR^3$, or N;
$R^4$ is chloro, cyano, hydroxyl, or trifluoromethyl;
each $R^5$ is independently halogen, cyano, hydroxyl, C1-C6 alkyl, or C1-C6 haloalkyl; and
m and n are independently 0, 1, 2, or 3.

In some embodiments of Formula (I), or a pharmaceutically acceptable salt thereof:
$R^1$ is hydrogen or C1-C6 alkyl;
$R^2$ is C1-C8 alkyl, C1-C8 haloalkyl, C3-C8 cycloalkyl, or —$NR^AR^B$;
$R^A$ and $R^B$ are independently hydrogen or C1-C6 alkyl, or $R^A$ and $R^B$ together with the nitrogen atom to which they are attached form a 4-6 membered heterocyclyl, wherein the 4-6 membered heterocyclyl is not N-piperazine;
each $R^3$ is independently halogen, cyano, hydroxyl, or C1-C6 alkyl;
X is CH, $CR^3$, or N;
$R^4$ is chloro, cyano, hydroxyl, or trifluoromethyl;
each $R^5$ is independently halogen, cyano, hydroxyl, C1-C6 alkyl, or C1-C6 haloalkyl; and
m and n are independently 0, 1, 2, or 3.

In some embodiments of Formula (I), or a pharmaceutically acceptable salt thereof:
$R^1$ is hydrogen or C1-C6 alkyl;
$R^2$ is C1-C8 alkyl, C1-C8 haloalkyl, C3-C8 cycloalkyl, or —$NR^AR^B$;
$R^A$ and $R^B$ are independently hydrogen or C1-C6 alkyl;
each $R^3$ is independently halogen, cyano, hydroxyl, or C1-C6 alkyl;
X is CH, $CR^3$, or N;
$R^4$ is chloro, cyano, hydroxyl, or trifluoromethyl;
each $R^5$ is independently halogen, cyano, hydroxyl, C1-C6 alkyl, or C1-C6 haloalkyl; and
m and n are independently 0, 1, 2, or 3.

In some embodiments, Formula (I), or a pharmaceutically acceptable salt thereof, is not a compound selected from the group consisting of:

[chemical structure]

[chemical structure]

[chemical structure]

[chemical structure]

or a pharmaceutically acceptable salt of any of the foregoing.

In some embodiments, $R^1$ is C1-C6 alkyl. In some embodiments, $R^1$ is methyl.
In some embodiments, $R^1$ is hydrogen.
In some embodiments, $R^2$ is C1-C8 alkyl. In some embodiments, $R^2$ is C3-C5 alkyl. In some embodiments, $R^2$ is isobutyl.
In some embodiments, $R^2$ is C1-C8 haloalkyl.
In some embodiments, $R^2$ is C3-C8 cycloalkyl.
In some embodiments, $R^2$ is C3-C5 cycloalkyl.
In some embodiments, $R^2$ is —$NR^AR^B$.
In some embodiments, $R^A$ is C1-C6 alkyl. In some embodiments, $R^A$ is methyl.
In some embodiments, $R^A$ is hydrogen.
In some embodiments, $R^B$ is C1-C6 alkyl. In some embodiments, $R^B$ is methyl.
In some embodiments, $R^B$ is hydrogen.
In some embodiments, $R^A$ and $R^B$ are the same. In some embodiments, $R^A$ and $R^B$ are different. In some embodiments, one of $R^A$ and $R^B$ is hydrogen and the other of $R^A$ and $R^B$ is C1-C6 alkyl. In some embodiments, one of $R^A$ and $R^B$ is hydrogen and the other of $R^A$ and $R^B$ is methyl.
In some embodiments, $R^A$ and $R^B$ together with the nitrogen atom to which they are attached form a 4-6 membered heterocyclyl.
In some embodiments, m is 1. In some embodiments, when m is 1, $R^3$ is ortho to X. In some embodiments, when m is 1, $R^3$ is meta to X.
In some embodiments, $R^3$ is halogen. In some embodiments, $R^3$ is chloro. In some embodiments, $R^3$ is fluoro.
In some embodiments, $R^3$ is cyano.
In some embodiments, $R^3$ is hydroxyl.
In some embodiments, $R^3$ is C1-C6 alkyl. In some embodiments, $R^3$ is methyl.
In some embodiments, X is $CR^3$.
In some embodiments, X is CH.
In some embodiments, X is N.
In some embodiments, m is 0. In some embodiments, m is 2. In some embodiments, m is 3.
In some embodiments, $R^4$ is chloro.
In some embodiments, $R^4$ is cyano.
In some embodiments, $R^4$ is hydroxyl.
In some embodiments, $R^4$ is trifluoromethyl.
In some embodiments, n is 1. In some embodiments, when n is 1, $R^5$ is ortho to $R^4$. In some embodiments, when n is 1, $R^5$ is meta to $R^4$.
In some embodiments, $R^5$ is halogen. In some embodiments, $R^5$ is chloro. In some embodiments, $R^5$ is fluoro.
In some embodiments, $R^5$ is cyano.
In some embodiments, $R^5$ is hydroxyl.
In some embodiments, $R^5$ is C1-C6 alkyl. In some embodiments, $R^5$ is methyl.
In some embodiments, $R^5$ is C1-C6 haloalkyl. In some embodiments, $R^5$ is trifluoromethyl.

In some embodiments, m and n are both 0. In some embodiments, m is 1 and n is 0. In some embodiments, m is 0 and n is 1.

In some embodiments, n is 0 and $R^4$ is chloro. In some embodiments, n is 0, $R^4$ is chloro, and $R^1$ is hydrogen. In some embodiments, n is 0, $R^4$ is chloro, and $R^1$ is methyl.

In some embodiments, m is 0 and X is N. In some embodiments, m is 0, X is N, and $R^1$ is hydrogen. In some embodiments, m is 0, X is N, and $R^1$ is methyl.

In some embodiments, m is 0, n is 1, $R^5$ is fluoro, and $R^4$ is chloro.

In some embodiments, $R^2$ is isobutyl, n is 0 or 1, m is 0 or 1, and X is N. In some embodiments, $R^2$ is isobutyl, n is 0, m is 0, and X is N. In some embodiments, $R^2$ is isobutyl, n is 1, m is 0, and X is N. In some embodiments, $R^2$ is isobutyl, n is 0, m is 1, and X is N. In some embodiments, $R^2$ is isobutyl, n is 1, m is 1, and X is N.

Some embodiments provide a compound selected from the group consisting of:

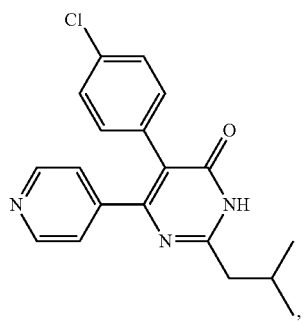 [SMILES: CC(C)Cc1nc(-c2ccncc2)c(-c2ccc(Cl)cc2)c(=O)[nH]1]

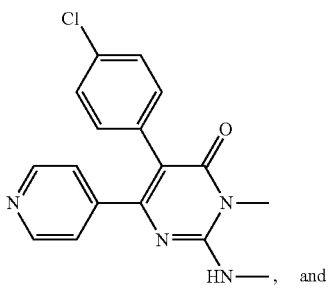, and

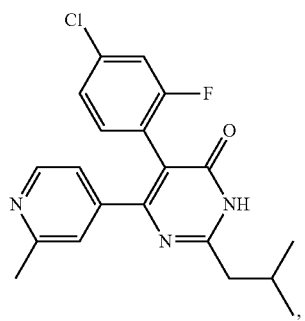

or a pharmaceutically acceptable salt of any of the foregoing.

Some embodiments provide a compound which is 5-(4-chlorophenyl)-2-isobutyl-6-(pyridin-4-yl)pyrimidin-4(3H)-one, or a pharmaceutically acceptable salt thereof, having the structure of

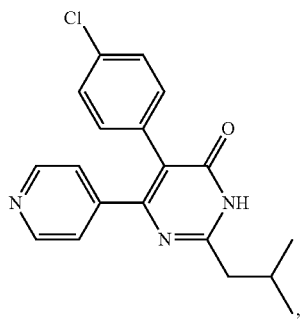

or a pharmaceutically acceptable salt thereof.

Some embodiments provide a compound which is 5-(4-chlorophenyl)-3-methyl-2-(methylamino)-6-(pyridin-4-yl)pyrimidin-4(3H)-one, or a pharmaceutically acceptable salt thereof, having the structure of

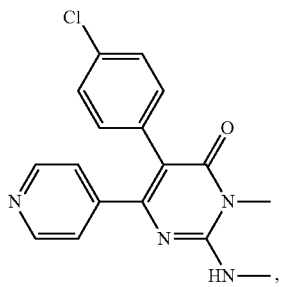 [SMILES: CNc1nc(-c2ccncc2)c(-c2ccc(Cl)cc2)c(=O)n1C]

or a pharmaceutically acceptable salt thereof.

Some embodiments provide a compound which is 5-(4-chloro-2-fluorophenyl)-2-isobutyl-6-(2-methylpyridin-4-yl)pyrimidin-4(3H)-one, or a pharmaceutically acceptable salt thereof, having the structure of

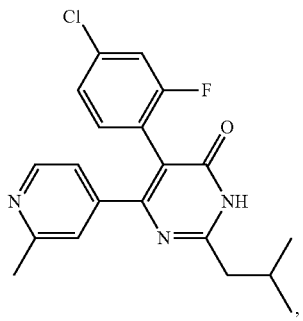 [SMILES: Cc1cc(-c2nc(CC(C)C)[nH]c(=O)c2-c2ccc(Cl)cc2F)ccn1]

or a pharmaceutically acceptable salt thereof.

In some embodiments, the compound of Formula (I), or a pharmaceutically acceptable salt thereof, is a compound of Formula (I-A):

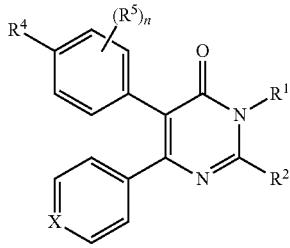

(I-A)

or a pharmaceutically acceptable salt thereof, wherein:
$R^1$ is hydrogen or C1-C6 alkyl;
$R^2$ is C1-C8 alkyl, C1-C8 haloalkyl, C3-C8 cycloalkyl, or —$NR^AR^B$;
$R^A$ and $R^B$ are independently hydrogen or C1-C6 alkyl, or $R^A$ and $R^B$ together with the nitrogen atom to which they are attached form a 4-6 membered heterocyclyl;
X is CH, $CR^3$, or N;
$R^4$ is chloro, cyano, hydroxyl, or trifluoromethyl;
each $R^5$ is independently halogen, cyano, hydroxyl, C1-C6 alkyl, or C1-C6 haloalkyl; and
n is 0 or 1.

In some embodiments, the compound of Formula (I), or a pharmaceutically acceptable salt thereof, is a compound of Formula (I-B):

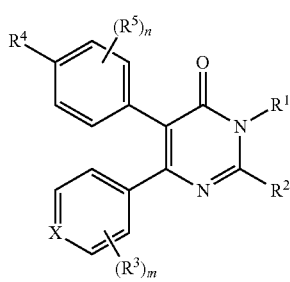

(I-B)

or a pharmaceutically acceptable salt thereof, wherein:
$R^1$ is hydrogen or methyl;
$R^2$ is C1-C8 alkyl;
each $R^3$ is independently halogen, cyano, hydroxyl, or C1-C6 alkyl; X is CH, $CR^3$, or N;
$R^4$ is chloro, cyano, hydroxyl, or trifluoromethyl;
each $R^5$ is independently halogen, cyano, hydroxyl, C1-C6 alkyl, or C1-C6 haloalkyl; and
m and n are independently 0 or 1.

In some embodiments, the compound of Formula (I), or a pharmaceutically acceptable salt thereof, is a compound of Formula (I-C)

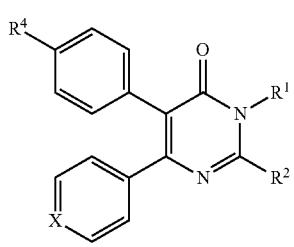

(I-C)

or a pharmaceutically acceptable salt thereof, wherein:
$R^1$ is hydrogen or C1-C6 alkyl;
$R^2$ is C1-C8 alkyl, C1-C8 haloalkyl, C3-C8 cycloalkyl, or —$NR^AR^B$;
$R^A$ and $R^B$ are independently hydrogen or C1-C6 alkyl, or $R^A$ and $R^B$ together with the nitrogen atom to which they are attached form a 4-6 membered heterocyclyl;
X is CH, $CR^3$, or N; and
$R^4$ is chloro, cyano, hydroxyl, or trifluoromethyl.

In some embodiments, the compound of Formula (I), or a pharmaceutically acceptable salt thereof, is a compound of Formula (I-D):

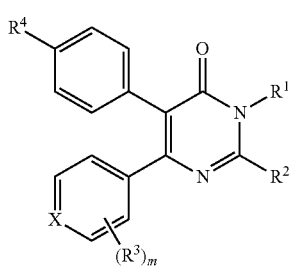

(I-D)

or a pharmaceutically acceptable salt thereof, wherein:
$R^1$ is hydrogen or C1-C6 alkyl;
$R^2$ is C1-C8 alkyl, C1-C8 haloalkyl, C3-C8 cycloalkyl, or —$NR^AR^B$;
$R^A$ and $R^B$ are independently hydrogen or C1-C6 alkyl, or $R^A$ and $R^B$ together with the nitrogen atom to which they are attached form a 4-6 membered heterocyclyl;
each $R^3$ is independently halogen, cyano, hydroxyl, or C1-C6 alkyl;
X is CH, $CR^3$, or N;
$R^4$ is chloro, cyano, hydroxyl, or trifluoromethyl; and
m is 0, 1, 2, or 3.

Pharmaceutical Compositions

Some embodiments provide a pharmaceutical composition comprising a compound of Formula (I), or a pharmaceutically acceptable salt thereof, and one or more pharmaceutically acceptable excipients.

In some embodiments, the compound of Formula (I), or a pharmaceutically acceptable salt thereof, is 5-(4-chlorophenyl)-2-isobutyl-6-(pyridin-4-yl)pyrimidin-4(3H)-one, 5-(4-chlorophenyl)-2-isobutyl-6-(pyridin-4-yl)pyrimidin-4(3H)-one, or 5-(4-chloro-2-fluorophenyl)-2-isobutyl-6-(2-methylpyridin-4-yl)pyrimidin-4(3H)-one, or a pharmaceutically acceptable salt of any of the foregoing.

Some embodiments provide a pharmaceutical composition comprising 5-(4-chlorophenyl)-2-isobutyl-6-(pyridin-4-yl)pyrimidin-4(3H)-one, or a pharmaceutically acceptable salt thereof, and one or more pharmaceutically acceptable excipients.

Some embodiments provide a pharmaceutical composition comprising 5-(4-chlorophenyl)-2-isobutyl-6-(pyridin-4-yl)pyrimidin-4(3H)-one, or a pharmaceutically acceptable salt thereof, and one or more pharmaceutically acceptable excipients.

Some embodiments provide a pharmaceutical composition comprising 5-(4-chloro-2-fluorophenyl)-2-isobutyl-6-(2-methylpyridin-4-yl)pyrimidin-4(3H)-one, a pharmaceutically acceptable salt thereof, and one or more pharmaceutically acceptable excipients.

In some embodiments, the amount of the compound of Formula (I), or a pharmaceutically acceptable salt thereof, in the pharmaceutical composition is a therapeutically effective amount.

Methods of Use

Provided herein are methods for inhibiting casein kinase 1 delta (CK-1δ), encoded by the CSNK1D gene. For example, provided herein are inhibitors of CK-1δ useful for treating or preventing diseases or disorders associated with dysregulation of a CSNK1D gene, a CK-1δ protein, or the expression or activity or level of any of the same (i.e., a CK-1δ-associated disease or disorder), such as neurological disorders (i.e., a CK-1δ-associated neurological disorder).

A "CK-1δ inhibitor" as used herein includes any compound exhibiting CK-1δ inactivation activity (e.g., inhibiting or decreasing).

The ability of test compounds to act as inhibitors of CK-1δ may be demonstrated by assays known in the art. The activity of the compounds and compositions provided herein as CK-1δ inhibitors can be assayed in vitro, in vivo, or in a cell line. In vitro assays include assays that determine inhibition of the kinase. Alternate in vitro assays quantitate the ability of the inhibitor to bind to the protein kinase and can be measured either by radio labeling the compound prior to binding, isolating the compound/kinase complex and determining the amount of radio label bound, or by running a competition experiment where new compounds are incubated with the kinase bound to known radio ligands.

In some embodiments, the compounds of Formula (I), or a pharmaceutically acceptable salt thereof, can selectively target CK-1δ. For example, a compound of Formula (I), or a pharmaceutically acceptable salt thereof, can selectively target CK-1δ over another kinase or non-kinase target.

Compounds of Formula (I), or pharmaceutically acceptable salts thereof (and pharmaceutical compositions comprising same), are useful for treating diseases and disorders which can be treated with a CK-1δ inhibitor, such as CK-1δ-associated diseases and disorders.

The term "CK-1δ-associated disease or disorder" as used herein refers to diseases or disorders associated with or having a dysregulation of a CSNK1D gene, a CK-1δ protein, or the expression or activity or level of any (e.g., one or more) of the same (e.g., any of the types of dysregulation of a CSNK1D gene, or a CK-1δ protein, or the expression or activity or level of any of the same described herein). Non-limiting examples of a CK-1δ-associated disease or disorder include, for example, CK-1δ-associated neurological disorders as described herein.

The term "CK-1δ-associated neurological disorders" as used herein refers to neurological disorders associated with or having a dysregulation of a CSNK1D gene, a CK-1δ protein, or expression or activity, or level of any of the same. Non-limiting examples of CK-1δ-associated neurological disorders include, for example, CK-1δ-associated neurological disorders such as amyotrophic lateral sclerosis (ALS), Alzheimer's disease, frontotemporal dementia (FTD), frontotemporal lobar degeneration with ubiquitin inclusions (FTLD-U), and limbic-predominant age-related TDP-43 encephalopathy (LATE).

The phrase "dysregulation of a CSNK1D gene, a CK-1δ protein, or the expression or activity or level of any of the same" refers to a genetic mutation (e.g., a mutation in a CSNK1D gene that results in the expression of a CK-1δ that includes a deletion of at least one amino acid as compared to a wild type CK-1δ, a mutation in a CSNK1D gene that results in the expression of CK-1δ with one or more point mutations as compared to a wild type CK-1δ, a mutation in a CSNK1D gene that results in the expression of CK-1δ with at least one inserted amino acid as compared to a wild type CK-1δ, a gene duplication that results in an increased level of CK-1δ in a cell, or a mutation in a regulatory sequence (e.g., a promoter and/or enhancer) that results in an increased level of CK-1δ in a cell), an alternative spliced version of CK-1δ mRNA that results in CK-1δ having a deletion of at least one amino acid in the CK-1δ as compared to the wild type CK-1δ), or increased expression (e.g., increased levels) of a wild type CK-1δ in a mammalian cell due to aberrant cell signaling (e.g., as compared to a control cell). As another example, a dysregulation of a CSNK1D gene, a CK-1δ protein, or expression or activity, or level of any of the same, can be a mutation in a CSNK1D gene that encodes a CK-1δ that is constitutively active or has increased activity as compared to a protein encoded by a CSNK1D gene that does not include the mutation.

Some embodiments provide a method of treating a CK-1δ-associated neurological disorder in a subject in need thereof, comprising administering to the subject, a therapeutically effective amount of a compound of Formula (I), or a pharmaceutically acceptable salt thereof.

Some embodiments provide a method of treating a CK-1δ-associated neurological disorder in a subject identified or diagnosed as having a CK-1δ-associated neurological disorder, comprising administering to the subject, a therapeutically effective amount of a compound of Formula (I), or a pharmaceutically acceptable salt thereof.

Some embodiments provide a method of treating a CK-1δ-associated neurological disorder in a subject determined to have a CK-1δ-associated neurological disorder, comprising administering to the subject, a therapeutically effective amount of a compound of Formula (I), or a pharmaceutically acceptable salt thereof.

Some embodiments provide a method of treating a CK-1δ-associated neurological disorder in a subject having a CK-1δ-associated neurological disorder, comprising administering to the subject, a therapeutically effective amount of a compound of Formula (I), or a pharmaceutically acceptable salt thereof.

Some embodiments provide a method of treating a CK-1δ-associated neurological disorder in a subject suspected as having a CK-1δ-associated neurological disorder, comprising administering to the subject, a therapeutically effective amount of a compound of Formula (I), or a pharmaceutically acceptable salt thereof.

Some embodiments provide a method of treating a CK-1δ-associated neurological disorder in a subject at risk of developing a CK-1δ-associated neurological disorder, comprising administering to the subject, a therapeutically effective amount of a compound of Formula (I), or a pharmaceutically acceptable salt thereof.

Some embodiments provide a method of treating a CK-1δ-associated neurological disorder in a subject exhibiting one or more symptoms of a CK-1δ-associated neurological disorder, comprising administering to the subject, a therapeutically effective amount of a compound of Formula (I), or a pharmaceutically acceptable salt thereof.

In some embodiments, the subject has been identified or diagnosed as having a dysregulation of a CSNK1D gene, a CK-1δ protein, or the expression or activity or level of any of the same (a CK-1δ-associated neurological disorder) (e.g., as determined using a regulatory agency-approved, e.g., FDA-approved, diagnostic method, assay, or kit).

In some embodiments, the subject has been identified or diagnosed as having aberrant phosphorylation of TDP-43. In some embodiments, the subject has been identified or diagnosed as having aggregates and/or inclusion bodies comprising TDP-43.

In some embodiments, the subject is suspected as having a CK-1δ-associated neurological disorder. In some embodiments, the subject has a clinical record indicating that the subject has a CK-1δ-associated neurological disorder (and optionally the clinical record indicates that the subject should be treated with a compound provided herein, or a pharmaceutically acceptable salt thereof).

In some embodiments, the subject is suspected as having aberrant phosphorylation of TDP-43. In some embodiments, the subject has a clinical record indicating that the subject has aberrant phosphorylation of TDP-43 (and optionally the clinical record indicates that the subject should be treated with a compound provided herein, or a pharmaceutically acceptable salt thereof).

In some embodiments, the subject is suspected as having aggregates and/or inclusion bodies comprising TDP-43. In some embodiments, the subject has a clinical record indicating that the subject has aggregates and/or inclusion bodies comprising TDP-43 (and optionally the clinical record indicates that the subject should be treated with a compound provided herein, or a pharmaceutically acceptable salt thereof).

Some embodiments provide a method of treating a CK-1δ-associated neurological disorder in a subject in need thereof, comprising (a) determining that the subject has a dysregulation of a CSNK1D gene, a CK-1δ protein, or the expression or activity or level of any of the same; and (b) administering to the subject, a therapeutically effective amount of a compound of Formula (I), or a pharmaceutically acceptable salt thereof.

Some embodiments provide a method of treating a CK-1δ-associated neurological disorder in a subject, comprising (a) determining that the subject has a dysregulation of a CSNK1D gene, a CK-1δ protein, or the expression or activity or level of any of the same; and (b) administering to the subject, a therapeutically effective amount of a compound of Formula (I), or a pharmaceutically acceptable salt thereof.

Some embodiments provide a method of treating a CK-1δ-associated neurological disorder in a subject, comprising (a) determining that the subject is exhibiting one or more symptoms of a CK-1δ-associated neurological disorder; and (b) administering to the subject, a therapeutically effective amount of a compound of Formula (I), or a pharmaceutically acceptable salt thereof.

Some embodiments provide a method of treating a CK-1δ-associated neurological disorder in a subject, comprising (a) determining that the subject is at risk of developing a CK-1δ-associated neurological disorder; (b) determining that the subject is exhibiting one or more symptoms of a CK-1δ-associated neurological disorder; and (c) administering to the subject, a therapeutically effective amount of a compound of Formula (I), or a pharmaceutically acceptable salt thereof.

In some embodiments, the CK-1δ-associated neurological disorder is ALS, Alzheimer's disease, FTD, FTLD-U, or LATE. In some embodiments, the CK-1δ-associated neurological disorder is ALS, Alzheimer's disease, FTD, or LATE.

In some embodiments, the CK-1δ-associated neurological disorder is ALS. ALS can be classified as familial or sporadic, depending on whether or not there is a family history of the disease. Familial ALS may account for 5% to 20%. More than 20 genes have been associated with familial ALS, of which four account for the majority of familial cases: C9orf72 (40%), SOD1 (20%), FUS (1-5%), and TARDBP (1-5%). The genetics of familial ALS are better understood than the genetics of sporadic ALS. The known ALS genes explain about 70% of familial ALS and about 15% of sporadic ALS. Overall, first-degree relatives of an individual with ALS have a 1% risk of developing ALS. ALS has an oligogenic mode of inheritance, meaning that mutations in two or more genes may contribute to causing the disease.

In sporadic ALS, there is no family history of the disease. Sporadic ALS and familial ALS appear identical clinically and pathologically and are similar genetically. About 10% of people having sporadic ALS have mutations in genes that are known to cause familial ALS.

In some embodiments, the CK-1δ-associated neurological disorder is Alzheimer's disease.

In some embodiments, the CK-1δ-associated neurological disorder is FTD.

In some embodiments, the CK-1δ-associated neurological disorder is FTD-U.

In some embodiments, the CK-1δ-associated neurological disorder is LATE.

Some embodiments provide a method of treating ALS in a subject in need thereof, comprising administering to the subject, a therapeutically effective amount of a compound of Formula (I), or a pharmaceutically acceptable salt thereof. In some embodiments, the subject is suspected of having ALS.

Some embodiments provide a method of reducing one or more symptoms of ALS in a subject in need thereof, comprising administering to the subject, a therapeutically effective amount of a compound of Formula (I), or a pharmaceutically acceptable salt thereof. In some embodiments, the one or more symptoms comprise muscle weakness, atrophy, muscle spasms throughout the body due to the degeneration of the upper motor and lower motor neurons, loss of the ability to initiate and control all voluntary movement, cognitive or behavioral dysfunction, frontotemporal dementia (FTD), language dysfunction, executive dysfunction, troubles with social cognition and verbal memory, neuropathic pain, spasticity, muscle cramps, contractures (permanent shortening of a muscle or joint), neck pain, back pain, shoulder pain, pressure ulcers, or any combination thereof. In some embodiments, the one or more symptoms are selected from the group consisting of muscle weakness, atrophy, muscle spasms throughout the body due to the degeneration of the upper motor and lower motor neurons, loss of the ability to initiate and control all voluntary movement, cognitive or behavioral dysfunction, frontotemporal dementia (FTD), language dysfunction, executive dysfunction, troubles with social cognition and verbal memory, neuropathic pain, spasticity, muscle cramps, contractures (permanent shortening of a muscle or joint), neck pain, back pain, shoulder pain, pressure ulcers, or any combination thereof. In some embodiments, the one or more symptoms are one, two, or three symptoms.

Some embodiments provide a method of treating FTD in a subject in need thereof, comprising administering to the subject, a therapeutically effective amount of a compound of Formula (I), or a pharmaceutically acceptable salt thereof. In some embodiments, the subject is suspected of having FTD.

Some embodiments provide a method of reducing one or more symptoms of FTD in a subject in need thereof, comprising administering to the subject, a therapeutically effective amount of a compound of Formula (I), or a pharmaceutically acceptable salt thereof. In some embodiments, the one or more symptoms comprise inappropriate social behavior, loss of empathy and other interpersonal skills, such as having sensitivity to another's feelings, lack of judgment, loss of inhibition, lack of interest (apathy), repetitive compulsive behavior, such as tapping, clapping or smacking lips, decline in personal hygiene, changes in eating habits, usually overeating or developing a preference for sweets and carbohydrates, eating inedible objects, compulsively wanting to put things in the mouth, increasing difficulty in using and understanding written and spoken language, such as having trouble finding the right word to use in speech or naming objects, trouble naming things, possibly replacing a specific word with a more general word such as "it", no longer knowing word meanings, having hesitant speech that may sound telegraphic, tremor, rigidity, muscle spasms or twitches, poor coordination, difficulty swallowing, muscle weakness, inappropriate laughing or crying, falls or walking problems, or any combination thereof. In some embodiments, the one or more symptoms are selected from the group consisting of inappropriate social behavior, loss of empathy and other interpersonal skills, such as having sensitivity to another's feelings, lack of judgment, loss of inhibition, lack of interest (apathy), repetitive compulsive behavior, such as tapping, clapping or smacking lips, decline in personal hygiene, changes in eating habits, usually overeating or developing a preference for sweets and carbohydrates, eating inedible objects, compulsively wanting to put things in the mouth, increasing difficulty in using and understanding written and spoken language, such as having trouble finding the right word to use in speech or naming objects, trouble naming things, possibly replacing a specific word with a more general word such as "it", no longer knowing word meanings, having hesitant speech that may sound telegraphic, tremor, rigidity, muscle spasms or twitches, poor coordination, difficulty swallowing, muscle weakness, inappropriate laughing or crying, falls or walking problems, or any combination thereof. In some embodiments, the one or more symptoms are one, two, or three symptoms.

Some embodiments provide a method of treating FTD-U in a subject in need thereof, comprising administering to the subject, a therapeutically effective amount of a compound of Formula (I), or a pharmaceutically acceptable salt thereof. In some embodiments, the subject is suspected of having FTD-U.

Some embodiments provide a method of reducing one or more symptoms of FTD-U in a subject in need thereof, comprising administering to the subject, a therapeutically effective amount of a compound of Formula (I), or a pharmaceutically acceptable salt thereof. In some embodiments, the one or more symptoms comprise inappropriate social behavior, loss of empathy and other interpersonal skills, such as having sensitivity to another's feelings, lack of judgment, loss of inhibition, lack of interest (apathy), repetitive compulsive behavior, such as tapping, clapping or smacking lips, decline in personal hygiene, changes in eating habits, usually overeating or developing a preference for sweets and carbohydrates, eating inedible objects, compulsively wanting to put things in the mouth, increasing difficulty in using and understanding written and spoken language, such as having trouble finding the right word to use in speech or naming objects, trouble naming things, possibly replacing a specific word with a more general word such as "it", no longer knowing word meanings, having hesitant speech that may sound telegraphic, tremor, rigidity, muscle spasms or twitches, poor coordination, difficulty swallowing, muscle weakness, inappropriate laughing or crying, falls or walking problems, or any combination thereof. In some embodiments, the one or more symptoms are selected from the group consisting of inappropriate social behavior, loss of empathy and other interpersonal skills, such as having sensitivity to another's feelings, lack of judgment, loss of inhibition, lack of interest (apathy), repetitive compulsive behavior, such as tapping, clapping or smacking lips, decline in personal hygiene, changes in eating habits, usually overeating or developing a preference for sweets and carbohydrates, eating inedible objects, compulsively wanting to put things in the mouth, increasing difficulty in using and understanding written and spoken language, such as having trouble finding the right word to use in speech or naming objects, trouble naming things, possibly replacing a specific word with a more general word such as "it", no longer knowing word meanings, having hesitant speech that may sound telegraphic, tremor, rigidity, muscle spasms or twitches, poor coordination, difficulty swallowing, muscle weakness, inappropriate laughing or crying, falls or walking problems, or any combination thereof. In some embodiments, the one or more symptoms are one, two, or three symptoms.

Some embodiments provide a method of treating LATE in a subject in need thereof, comprising administering to the subject, a therapeutically effective amount of a compound of Formula (I), or a pharmaceutically acceptable salt thereof. In some embodiments, the subject is suspected of having LATE.

Some embodiments provide a method of reducing one or more symptoms of LATE in a subject in need thereof, comprising administering to the subject, a therapeutically effective amount of a compound of Formula (I), or a pharmaceutically acceptable salt thereof. In some embodiments, the one or more symptoms comprise wandering or getting lost, making poor decisions, misplacing things, having trouble driving, having difficulty maintaining personal hygiene, difficulty dressing, difficulty cooking, difficulty paying bills, mental decline, or any combination thereof. In some embodiments, the one or more symptoms are selected from the group consisting of wandering or getting lost, making poor decisions, misplacing things, having trouble driving, having difficulty maintaining personal hygiene, difficulty dressing, difficulty cooking, difficulty paying bills, mental decline, or any combination thereof. In some embodiments, the one or more symptoms are one, two, or three symptoms.

Some embodiments provide a method of treating Alzheimer's disease in a subject in need thereof, comprising administering to the subject, a therapeutically effective amount of a compound of Formula (I), or a pharmaceutically acceptable salt thereof. In some embodiments, the subject is suspected of having Alzheimer's disease.

Some embodiments provide a method of reducing one or more symptoms of Alzheimer's disease in a subject in need thereof, comprising administering to the subject, a therapeutically effective amount of a compound of Formula (I), or a pharmaceutically acceptable salt thereof. In some embodiments, the one or more symptoms comprise memory loss, misplacing items, forgetting the names of places and objects, becoming less flexible and more hesitant to try new things, confusion and disorientation, obsessive, repetitive, or impulsive behavior, delusions, aphasia, mood swings, depression, anxiety, agnosia, akinesia, weight loss, gradual loss of speech, significant problems with short and long-term memory, or any combination thereof. In some embodiments, the one or more symptoms are selected from the group consisting of memory loss, misplacing items, forgetting the names of places and objects, becoming less flexible and more hesitant to try new things, confusion and disorientation, obsessive, repetitive, or impulsive behavior, delusions, aphasia, mood swings, depression, anxiety, agnosia, akinesia, weight loss, gradual loss of speech, significant problems with short and long-term memory, or any combination thereof. In some embodiments, the one or more symptoms are one, two, or three symptoms.

Some embodiments provide a method of treating ALS in a subject in need thereof, comprising administering to the subject a therapeutically effective amount of a compound selected from the group consisting of:

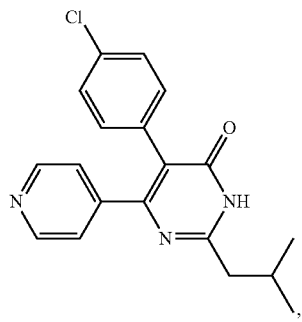 [SMILES: CC(C)Cc1nc(-c2ccncc2)c(-c2ccc(Cl)cc2)c(=O)[nH]1]

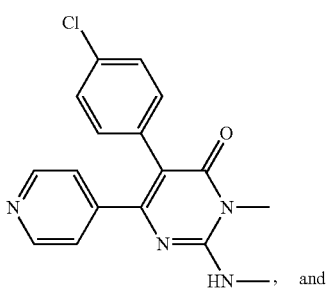

and

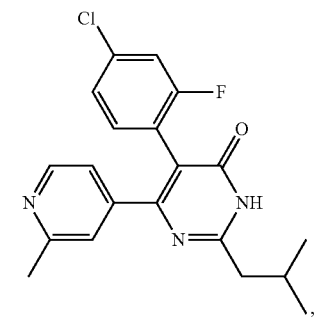

or a pharmaceutically acceptable salt of any of the foregoing.

Some embodiments provide a method of treating ALS in a subject in need thereof, comprising administering to the subject a therapeutically effective amount of a compound which is 5-(4-chlorophenyl)-2-isobutyl-6-(pyridin-4-yl)pyrimidin-4(3H)-one, or a pharmaceutically acceptable salt thereof, having the structure of

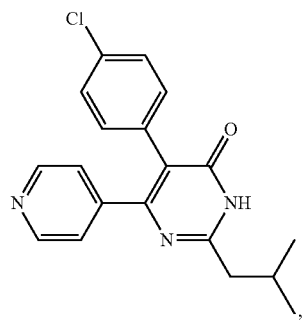

or a pharmaceutically acceptable salt thereof.

Some embodiments provide a method of treating ALS in a subject in need thereof, comprising administering to the subject a therapeutically effective amount of a compound which is 5-(4-chlorophenyl)-3-methyl-2-(methylamino)-6-(pyridin-4-yl)pyrimidin-4(3H)-one, or a pharmaceutically acceptable salt thereof, having the structure of

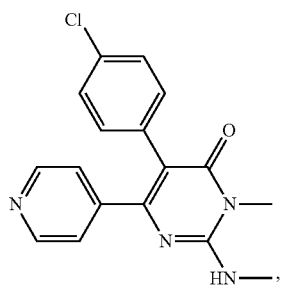 [SMILES: CNc1nc(-c2ccncc2)c(-c2ccc(Cl)cc2)c(=O)n1C]

or a pharmaceutically acceptable salt thereof.

Some embodiments provide a method of treating ALS in a subject in need thereof, comprising administering to the subject a therapeutically effective amount of a compound which is 5-(4-chloro-2-fluorophenyl)-2-isobutyl-6-(2-methylpyridin-4-yl)pyrimidin-4(3H)-one, or a pharmaceutically acceptable salt thereof, having the structure of

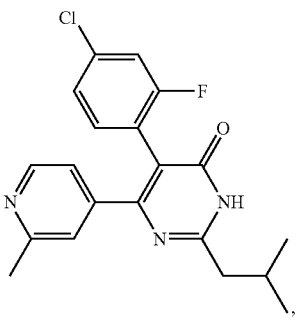

or a pharmaceutically acceptable salt thereof.

Some embodiments provide a method of treating Alzheimer's disease in a subject in need thereof, comprising administering to the subject a therapeutically effective amount of a compound selected from the group consisting of:

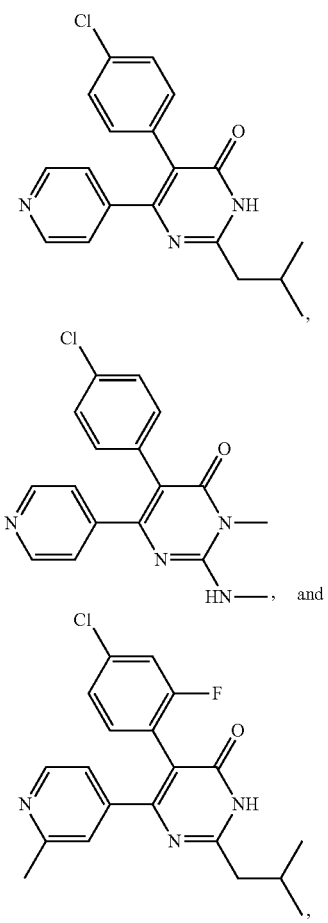

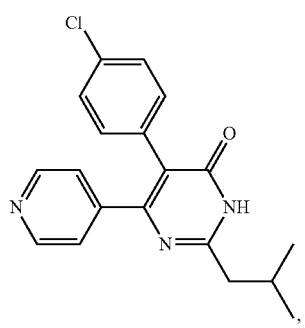, and

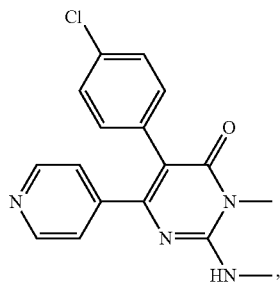 [SMILES: CNc1nc(-c2ccncc2)c(-c2ccc(Cl)cc2)c(=O)n1C]

or a pharmaceutically acceptable salt of any of the foregoing.

Some embodiments provide a method of treating Alzheimer's disease in a subject in need thereof, comprising administering to the subject a therapeutically effective amount of a compound which is 5-(4-chlorophenyl)-2-isobutyl-6-(pyridin-4-yl)pyrimidin-4(3H)-one, or a pharmaceutically acceptable salt thereof, having the structure of

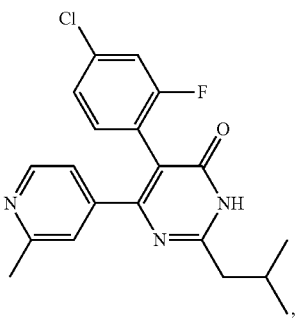

or a pharmaceutically acceptable salt thereof.

Some embodiments provide a method of treating Alzheimer's disease in a subject in need thereof, comprising administering to the subject a therapeutically effective amount of a compound which is 5-(4-chlorophenyl)-3-methyl-2-(methylamino)-6-(pyridin-4-yl)pyrimidin-4(3H)-one, or a pharmaceutically acceptable salt thereof, having the structure of

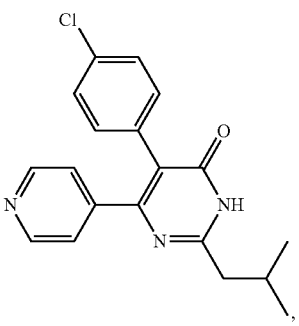 [SMILES: CC(C)Cc1nc(-c2ccncc2)c(-c2ccc(Cl)cc2)c(=O)[nH]1]

or a pharmaceutically acceptable salt thereof.

Some embodiments provide a method of treating Alzheimer's disease in a subject in need thereof, comprising administering to the subject a therapeutically effective amount of a compound which is 5-(4-chloro-2-fluorophenyl)-2-isobutyl-6-(2-methylpyridin-4-yl)pyrimidin-4(3H)-one, or a pharmaceutically acceptable salt thereof, having the structure of

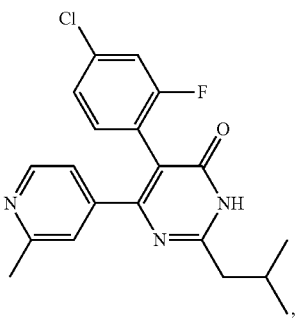

or a pharmaceutically acceptable salt thereof.

Some embodiments provide a method of treating FTD in a subject in need thereof, comprising administering to the subject a therapeutically effective amount of a compound selected from the group consisting of:

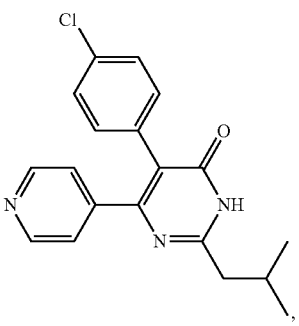 [SMILES: CC(C)Cc1nc(-c2ccncc2)c(-c2ccc(Cl)cc2)c(=O)[nH]1]

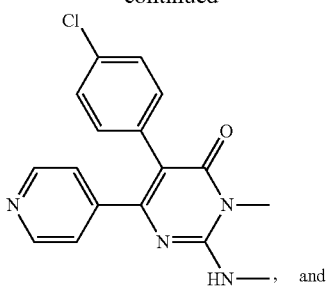

and

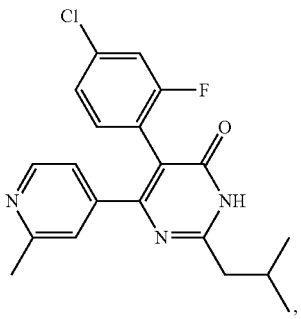

or a pharmaceutically acceptable salt of any of the foregoing.

Some embodiments provide a method of treating FTD in a subject in need thereof, comprising administering to the subject a therapeutically effective amount of a compound which is 5-(4-chlorophenyl)-2-isobutyl-6-(pyridin-4-yl)pyrimidin-4(3H)-one, or a pharmaceutically acceptable salt thereof, having the structure of

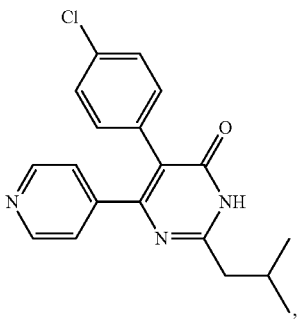

or a pharmaceutically acceptable salt thereof.

Some embodiments provide a method of treating FTD in a subject in need thereof, comprising administering to the subject a therapeutically effective amount of a compound which is 5-(4-chlorophenyl)-3-methyl-2-(methylamino)-6-(pyridin-4-yl)pyrimidin-4(3H)-one, or a pharmaceutically acceptable salt thereof, having the structure of

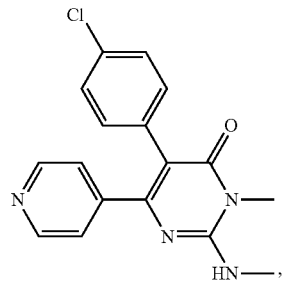 [SMILES: CNc1nc(-c2ccncc2)c(-c2ccc(Cl)cc2)c(=O)n1C]

or a pharmaceutically acceptable salt thereof.

Some embodiments provide a method of treating FTD in a subject in need thereof, comprising administering to the subject a therapeutically effective amount of a compound which is 5-(4-chloro-2-fluorophenyl)-2-isobutyl-6-(2-methylpyridin-4-yl)pyrimidin-4(3H)-one, or a pharmaceutically acceptable salt thereof, having the structure of

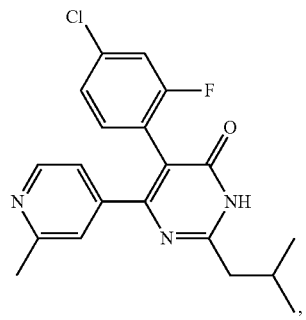 [SMILES: Cc1cc(-c2nc(CC(C)C)[nH]c(=O)c2-c2ccc(Cl)cc2F)ccn1]

or a pharmaceutically acceptable salt thereof.

Some embodiments provide a method of treating FTLD-U in a subject in need thereof, comprising administering to the subject a therapeutically effective amount of a compound selected from the group consisting of:

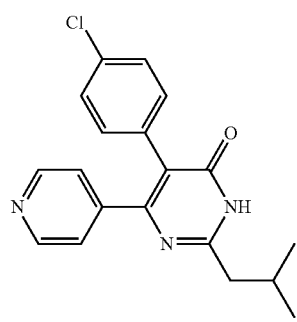

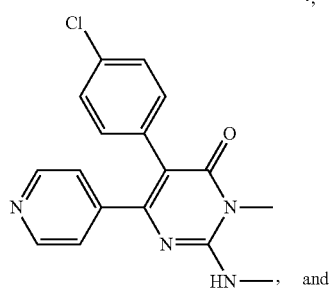

and

-continued

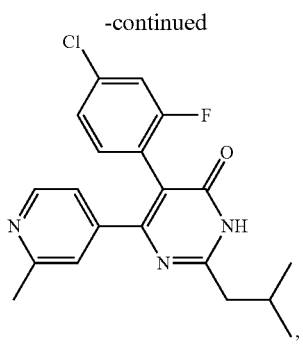

or a pharmaceutically acceptable salt of any of the foregoing.

Some embodiments provide a method of treating FTLD-U in a subject in need thereof, comprising administering to the subject a therapeutically effective amount of a compound which is 5-(4-chlorophenyl)-2-isobutyl-6-(pyridin-4-yl)pyrimidin-4(3H)-one, or a pharmaceutically acceptable salt thereof, having the structure of

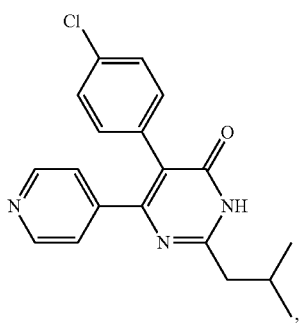 [SMILES: CC(C)Cc1nc(-c2ccncc2)c(-c2ccc(Cl)cc2)c(=O)[nH]1]

or a pharmaceutically acceptable salt thereof.

Some embodiments provide a method of treating FTLD-U in a subject in need thereof, comprising administering to the subject a therapeutically effective amount of a compound which is 5-(4-chlorophenyl)-3-methyl-2-(methylamino)-6-(pyridin-4-yl)pyrimidin-4(3H)-one, or a pharmaceutically acceptable salt thereof, having the structure of

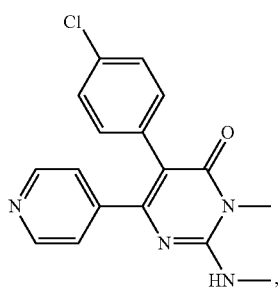 [SMILES: CNc1nc(-c2ccncc2)c(-c2ccc(Cl)cc2)c(=O)n1C]

or a pharmaceutically acceptable salt thereof.

Some embodiments provide a method of treating FTLD-U in a subject in need thereof, comprising administering to the subject a therapeutically effective amount of a compound which is 5-(4-chloro-2-fluorophenyl)-2-isobutyl-6-(2-methylpyridin-4-yl)pyrimidin-4(3H)-one, or a pharmaceutically acceptable salt thereof, having the structure of

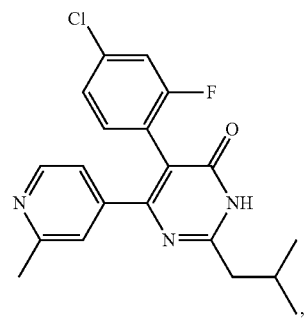 [SMILES: Cc1cc(-c2nc(CC(C)C)[nH]c(=O)c2-c2ccc(Cl)cc2F)ccn1]

or a pharmaceutically acceptable salt thereof.

Some embodiments provide a method of treating LATE in a subject in need thereof, comprising administering to the subject a therapeutically effective amount of a compound selected from the group consisting of:

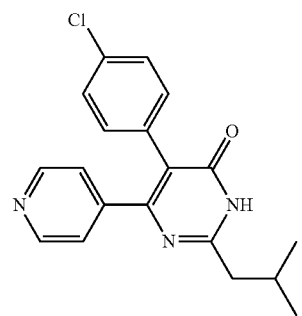

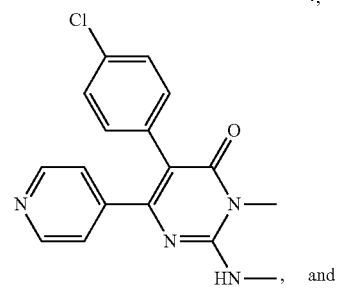

and

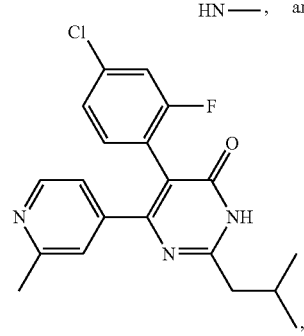

or a pharmaceutically acceptable salt of any of the foregoing.

Some embodiments provide a method of treating LATE in a subject in need thereof, comprising administering to the subject a therapeutically effective amount of a compound which is 5-(4-chlorophenyl)-2-isobutyl-6-(pyridin-4-yl)pyrimidin-4(3H)-one, or a pharmaceutically acceptable salt thereof, having the structure of

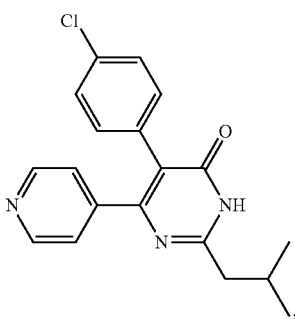 [SMILES: CC(C)Cc1nc(-c2ccncc2)c(-c2ccc(Cl)cc2)c(=O)[nH]1]

or a pharmaceutically acceptable salt thereof.

Some embodiments provide a method of treating LATE in a subject in need thereof, comprising administering to the subject a therapeutically effective amount of a compound which is 5-(4-chlorophenyl)-3-methyl-2-(methylamino)-6-(pyridin-4-yl)pyrimidin-4(3H)-one, or a pharmaceutically acceptable salt thereof, having the structure of

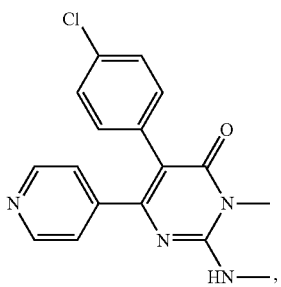 [SMILES: CNc1nc(-c2ccncc2)c(-c2ccc(Cl)cc2)c(=O)n1C]

or a pharmaceutically acceptable salt thereof.

Some embodiments provide a method of treating LATE in a subject in need thereof, comprising administering to the subject a therapeutically effective amount of a compound which is 5-(4-chloro-2-fluorophenyl)-2-isobutyl-6-(2-methylpyridin-4-yl)pyrimidin-4(3H)-one, or a pharmaceutically acceptable salt thereof, having the structure of

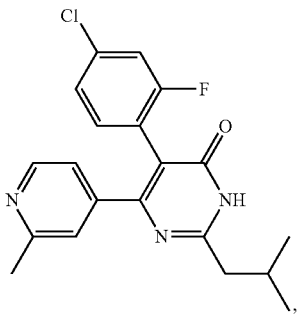 [SMILES: Cc1cc(-c2nc(CC(C)C)[nH]c(=O)c2-c2ccc(Cl)cc2F)ccn1]

or a pharmaceutically acceptable salt thereof.

The term "regulatory agency" refers to a country's agency for the approval of the medical use of pharmaceutical agents with the country. For example, a non-limiting example of a regulatory agency is the U.S. Food and Drug Administration (FDA).

Also provided is a method for inhibiting CK-1δ activity in a cell, comprising contacting the cell with a compound of Formula (I), or a pharmaceutically acceptable salt thereof.

Also provided is a method for inhibiting TDP-43 phosphorylation in a cell comprising TDP-43 and CK-1δ, the method comprising contacting the cell with a compound of Formula (I), or a pharmaceutically acceptable salt thereof.

Also provided is a method for inhibiting TDP-43 aggregation in a cell comprising TDP-43 and CK-1δ, the method comprising contacting the cell with a compound of Formula (I), or a pharmaceutically acceptable salt thereof.

In some embodiments, the contacting is in vitro. In some embodiments, the contacting is in vivo. In some embodiments, the contacting is in vivo. In some embodiments, the cell is in a sample from a subject, e.g., a subject at risk of developing a CK-1δ-associated neurological disorder.

In some embodiments, when the contacting is in vivo, the method comprises administering an effective amount of a compound of Formula (I), or a pharmaceutically acceptable salt thereof, to a subject having a cell having aberrant CK-1δ activity.

In some embodiments, when the contacting is in vivo, the method comprises administering an effective amount of a compound of Formula (I), or a pharmaceutically acceptable salt thereof. to a subject having a cell having aberrant TDP-43 phosphorylation.

In some embodiments, when the contacting is in vivo, the method comprises administering an effective amount of a compound of Formula (I), or a pharmaceutically acceptable salt thereof, to a subject having a cell having TDP-43 aggregation.

In some embodiments, the cell is a neural cell. In some embodiments, the cell is a mammalian neural cell.

As used herein, the term "contacting" refers to the bringing together of indicated moieties in an in vitro system or an in vivo system. For example, "contacting" a CK-1δ protein with a compound provided herein includes the administration of a compound provided herein to an individual or subject, such as a human, having a CK-1δ protein, as well as, for example, introducing a compound provided herein into a sample containing a cellular or purified preparation containing the CK-1δ protein.

In some embodiments, the compound of Formula (I) has a Kpuu of about 0.21 to about 0.46. In some embodiments, the compound of Formula (I) has a Kpuu of about 0.21 to about 0.33. In some embodiments, the compound of Formula (I) has a Kpuu of about 0.33 to about 0.46. In some embodiments, the compound of Formula (I) has a Kpuu of 0.21 to 0.46. In some embodiments, the compound of Formula (I) has a Kpuu of 0.21 to 0.33. In some embodiments, the compound of Formula (I) has a Kpuu of 0.33 to 0.46. In some embodiments, the compound of Formula (I) has a Kpuu of about 0.21, about 0.23, about 0.25, about 0.27, about 0.29, about 0.31, about 0.33, about 0.35, about 0.37, about 0.39, about 0.41, about 0.43, or about 0.46. In some embodiments, the compound of Formula (I) has a Kpuu of 0.21, 0.23, 0.25, 0.27, 0.29, 0.31, 0.33, 0.35, 0.37, 0.39, 0.41, 0.43, or 0.46.

When employed as pharmaceuticals, the compounds of Formula (I), including pharmaceutically acceptable salts thereof, can be administered in the form of pharmaceutical compositions as described herein.

EXAMPLES

The general methods for the preparation of the compounds of Formula (I) have been described in an illustrative manner and is intended to be description, rather than of limitation. Thus, it will be appreciated that conditions such as choice of solvent, temperature of reaction, volumes,

Example 1

5-(4-chlorophenyl)-3-methyl-2-(methylamino)-6-(pyridin-4-yl)pyrimidin-4(3H)-one (Compound 1)

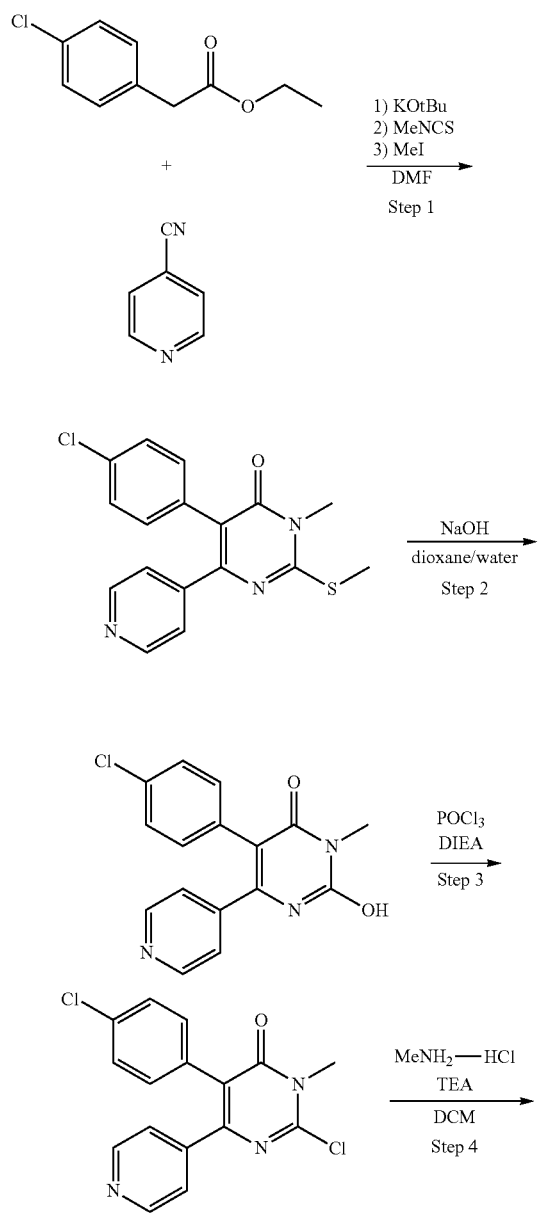

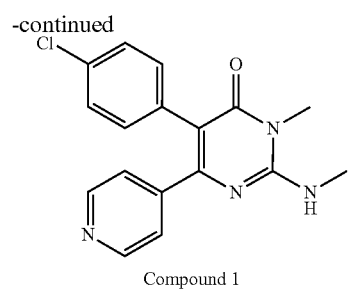

Compound 1

Step 1: 5-(4-chlorophenyl)-3-methyl-2-(methylthio)-6-(pyridin-4-yl)pyrimidin-4(3H)-one. To a stirred solution of ethyl 2-(4-chlorophenyl)acetate (10 g, 50.3 mmol) in DMF (130 mL) was added isonicotinonitrile (5.35 g, 51.3 mmol) and potassium tert-butoxide (51.3 mL, 51.3 mmol), and the reaction mixture was stirred at 25° C. After 1.5 hours, a solution of isothiocyanatomethane (4.45 g, 60.9 mmol) in DMF (2.6 mL) was added slowly to maintain the internal temperature below 25° C., and the reaction was stirred for 1 hour. The reaction mixture was then cooled below 5° C., and methyl iodide (3.21 mL, 51.3 mmol) was added. The reaction mixture was stirred at 25° C. for 1 hour. Water (170 mL) was added to the reaction slowly, to maintain the internal temperature below 10° C. and the reaction mixture was stirred overnight at 25° C. The white precipitate was collected by vacuum filtration, washed with water (100 mL), and dried in vacuo to provide 5-(4-chlorophenyl)-3-methyl-2-(methylthio)-6-(pyridin-4-yl)pyrimidin-4(3H)-one (8.2 g, 23.85 mmol, 47.4% yield) as a brown solid. MS (m/z) 343.9 [M+H].

Step 2: 5-(4-chlorophenyl)-2-hydroxy-3-methyl-6-(pyridin-4-yl)pyrimidin-4(3H)-one. To a stirred solution of 5-(4-chlorophenyl)-3-methyl-2-(methylthio)-6-(pyridin-4-yl)pyrimidin-4(3H)-one (240 g, 698 mmol) in 1,4-dioxane (205 mL) was added aqueous sodium hydroxide (582 mL, 3.50 mol) and the reaction mixture was stirred at 100° C. for 16 h. The reaction mixture was cooled to 25° C. and diluted with water (70 mL). The aqueous layer was washed with ethyl acetate, and the pH of the aqueous layer was adjusted to 4 with 1.5 N aqueous HCl (~20 mL). The precipitate was collected by vacuum filtration, washed with Petroleum ether, and dried in vacuo to provide 5-(4-chlorophenyl)-2-hydroxy-3-methyl-6-(pyridin-4-yl)pyrimidin-4(3H)-one as an off-white solid. MS (m/z) 313.9 [M+H].

Step 3: 2-chloro-5-(4-chlorophenyl)-3-methyl-6-(pyridin-4-yl)pyrimidin-4(3H)-one. To a stirred solution of 5-(4-chlorophenyl)-2-hydroxy-3-methyl-6-(pyridin-4-yl)pyrimidin-4(3H)-one (50 g, 159 mmol) in POCl₃ (500 mL, 5.36 mol) at 0° C. was added DIPEA (84 mL, 478 mmol) dropwise. The reaction mixture was then stirred at 110° C. for 16 hours, and concentrated. The residue was redissolved in dichloromethane (2.5 L) and reverse quenched in ice-water (2.0 L). The reaction mixture was basified with saturated NaHCO3 (1.0 L), and the organic layer washed with brine, dried over anhydrous Na2SO4, filtered and concentrated under reduced pressure to provide 143 g of the crude product. The crude material was triturated with DCM, collected by vacuum filtration, and dried in vacuo to provide 2-chloro-5-(4-chlorophenyl)-3-methyl-6-(pyridin-4-yl)pyrimidin-4(3H)-one (34 g, 102 mmol, 64.2% yield). MS (m/z) 332.0 [M+H].

Step 4: 5-(4-chlorophenyl)-3-methyl-2-(methylamino)-6-(pyridin-4-yl)pyrimidin-4(3H)-one. To a stirred solution of 2-chloro-5-(4-chlorophenyl)-3-methyl-6-(pyridin-4-yl)pyrimidin-4(3H)-one (20 g, 60.2 mmol) in dichloromethane (200 mL) at 0° C. was added methylamine hydrochloride (16.26 g, 241 mmol), followed by TEA (33.6 mL, 241 mmol) dropwise. The reaction was stirred at 40° C. overnight. After 16 hours, the reaction mixture was washed with water (200 mL), and brine (2×200 mL), dried over sodium sulfate, and concentrated in vacuo to obtain 18 g of the crude product. The crude material was triturated with DCM (100 mL) to obtain 5-(4-chlorophenyl)-3-methyl-2-(methylamino)-6-(pyridin-4-yl)pyrimidin-4(3H)-one (12 g, 36.7 mmol, 61.0% yield) as pale yellow solid. MS (m/z) 327.1 [M+H]. 1H NMR (600 MHZ, DMSO-d$^6$) δ 8.40-8.48 (m, 2H), 7.40 (br d, J=4.20 Hz, 1H), 7.24-7.30 (m, 2H), 7.15-7.21 (m, 2H), 7.02-7.10 (m, 2H), 3.35 (s, 3H), 2.91 (d, J=4.20 Hz, 3H).

Example 2

5-(4-chlorophenyl)-2-isobutyl-6-(pyridin-4-yl)pyrimidin-4(3H)-one (Compound 2)

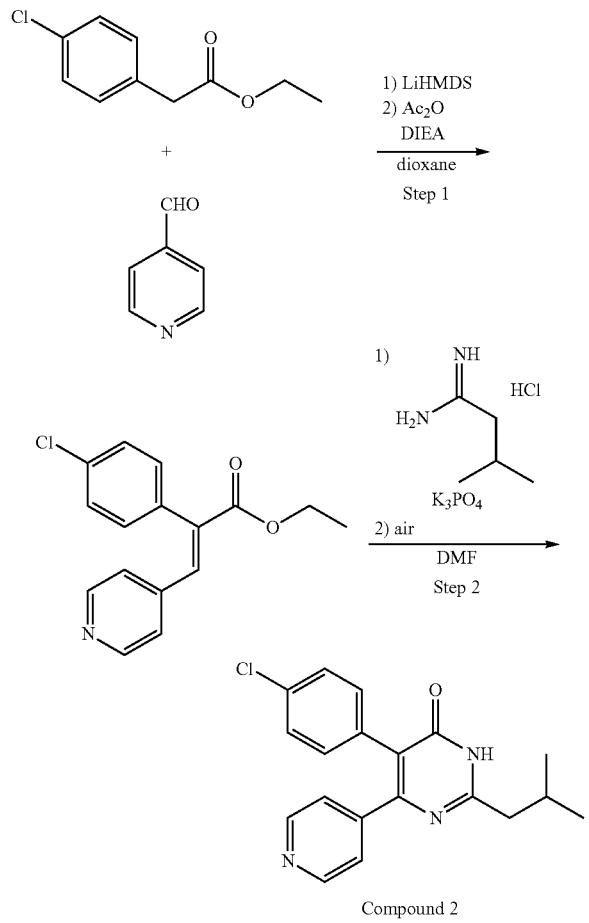

Compound 2

Step 1: ethyl (E)-2-(4-chlorophenyl)-3-(pyridin-4-yl) acrylate. To a stirred solution of ethyl 2-(4-chlorophenyl) acetate (10 g, 50.3 mmol) and isonicotinaldehyde (5.39 g, 50.3 mmol) in 1,4-dioxane (160 mL) at 0° C. was added lithium bis(trimethylsilyl)amide (76 mL, 76 mmol), and the reaction was stirred at ambient temperature. After 1 hour, DIEA (88 mL, 503 mmol) and acetic anhydride (85 mL, 906 mmol) were added. The reaction was stirred for 1 hour at ambient temperature, and then heated to 100° C. and stirred for 16 h. After 16 h, the reaction was partitioned between water and ethyl acetate. The organic layer was washed with water and brine, dried over anhydrous Na$_2$SO$_4$, filtered, and concentrated under reduced pressure. The crude was purified by column chromatography using 8% ethyl acetate in hexanes as an eluent to provide ethyl (E)-2-(4-chlorophenyl)-3-(pyridin-4-yl)acrylate (7 g, 24.33 mmol, 48.3% yield) as colourless liquid. MS (m/z) 288.1 [M+H].

Step 2: 5-(4-chlorophenyl)-2-isobutyl-6-(pyridin-4-yl)pyrimidin-4(3H)-one. To a solution of ethyl (E)-2-(4-chlorophenyl)-3-(pyridin-4-yl)acrylate (20.00 g, 69.5 mmol) in DMF (348 mL) was added 3-methylbutanimidamide hydrochloride (14.24 g, 104 mmol, Enamine) and potassium phosphate (32.5 g, 153 mmol, Aldrich), and the reaction was stirred at 110° C. After 6 hours, the flask was opened to the air and stirred overnight. After 16 hours, the reaction mixture was cooled to ambient temperature and extracted with ethyl acetate (3×200 mL). The combined organic layers were washed with water (10×100 mL), dried over anhydrous MgSO$_4$, filtered, and concentrated. The crude product was purified by column chromatography, eluting with 0-75% ethyl acetate in heptane, to provide 5-(4-chlorophenyl)-2-isobutyl-6-(pyridin-4-yl)pyrimidin-4(3H)-one (16.2 g, 47.8 mmol, 68.7% yield) as an off-white solid. MS (m/z) 340.0 [M+H]. $^1$H NMR (500 MHZ, DMSO-d$^6$) δ ppm 12.83 (br s, 1H), 8.47 (d, J=5.0 Hz, 2H), 7.33 (d, J=7.6 Hz, 2H), 7.13-7.21 (m, 4H), 2.18 (dquin, J=13.6, 6.8, 6.8, 6.8, 6.8 Hz, 1H), 0.97 (d, J=6.7 Hz, 6H).

Example 3

5-(4-chloro-2-fluorophenyl)-2-isobutyl-6-(2-methylpyridin-4-yl)pyrimidin-4(3H)-one (Compound 3)

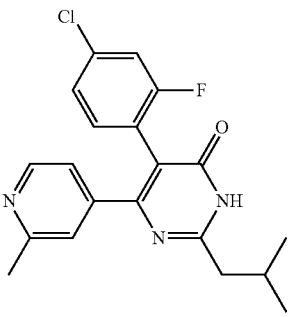 [SMILES: Cc1cc(-c2nc(CC(C)C)[nH]c(=O)c2-c2ccc(Cl)cc2F)ccn1]

Compound 3 was synthesized analogously to Compound 2, using ethyl 2-(4-chloro-2-fluorophenyl)acetate in Step 1. LCMS (ESI) [M+H]$^+$ m/z: calcd 371.12, found 372.0.

Assays

Cellular Target Engagement (NanoBRET)

The cell based CK-1δ target engagement assay is a NanoBRET competition assay that directly quantifies compound binding to full length kinases in live cells (Robers M et al. Nat. Comm. No 6 (2015)). The assay utilizes a cell permeable fluorescent tracer that reversibly binds to a NanoLuc-tagged kinase expressed in 293T-HEK cells. Intracellular target engagement of an unmodified test compound was measured by competitive displacement of the tracer resulting in a loss of bioluminescence energy transfer (BRET) that was quantified on a microplate-based luminometer.

Biochemical Kinase Assay

Biochemical inhibition of CK-1δ and kinome selectivity was assessed using a HotSpot radioisotope filter binding assay (Reaction Biology). In the HotSpot assay, compounds were incubated with the kinase, substrate, cofactors, and radioisotope-labeled ATP. The reaction mixtures are then spotted onto filter papers, which bind the radioisotope-labeled catalytic product that can be quantified.

The biological activity of certain compounds using the assays described above is shown in Table 2. The $IC_{50}$ ranges are as follows: for NanoBRET $IC_{50}$ (nM), A denotes <400 nM; B denotes 400 nM≤$K_D$<800 nM; C denotes $K_D$≥800 nM. For the biochemical kinase assay $IC_{50}$ (nM), A denotes <50 nM; B denotes 50 nM≤$IC_{50}$<100 nM; C denotes ≥100 nM.

TABLE 2

| Cpmd. No. | NanoBRET CK-1d $IC_{50}$ (nM) | Biochemical Kinase Assay CK-1d $IC_{50}$ (nM) |
| --- | --- | --- |
| 1 | B | A |
| 2 | A | A |
| 3 | A | B |

Plasma and Brain Binding Assays

Plasma and brain tissue binding of representative compounds of Formula (I) ("Compound A" and "Compound B") were determined using an equilibrium dialysis device. The compound and plasma or a brain tissue mixture was loaded into the donor side of the device and dialysis buffer was loaded into the receiver side of the device. The device was incubated at 37° C. with 5% $CO_2$ for 4 hours. After the incubation, the samples were aliquoted, analyzed by LC-MS/MS, and the concentrations were used to calculate the percent unbound shown in Tables 3 and 4.

TABLE 3

| | Compound A | | | |
| --- | --- | --- | --- | --- |
| Assay | Species | Approx % Recovery | AVG % Bound | AVG % Unbound |
| Plasma Protein Binding | Cyno | 103 | 88 | 12 |
| Plasma Protein Binding | Dog | 103 | 90 | 10 |
| Plasma Protein Binding | Human | 97 | 91 | 9 |
| Plasma Protein Binding | Mouse | 99 | 94 | 6 |
| Plasma Protein Binding | Minipig | 100 | 92 | 8 |
| Brain Tissue Binding | Rat | 96 | 93 | 7 |
| Plasma Protein Binding | Rat | 95 | 92 | 8 |

TABLE 4

| | Compound B | | | |
| --- | --- | --- | --- | --- |
| Assay | Species | Approx. % Recovery | AVG % Bound | AVG % Unbound |
| Plasma Protein Binding | Cyno | 95 | 95 | 5 |
| Plasma Protein Binding | Dog | 95 | 97 | 3 |
| Plasma Protein Binding | Human | 88 | 97 | 3 |
| Plasma Protein Binding | Mouse | 92 | 98 | 2 |
| Plasma Protein Binding | Minipig | 88 | 97 | 3 |
| Brain Tissue Binding | Rat | 93 | 98 | 2 |
| Plasma Protein Binding | Rat | 93 | 92 | 8 |

These data were used to calculate free brain to plasma ratios (Kpuu), which illustrates the extent of compound penetration into the brain. Compound A has a Kpuu in rats of about 0.22 and Compound B has a Kpuu in rats of about 0.46.

NUMBERED EMBODIMENTS

1. A compound of Formula (I).

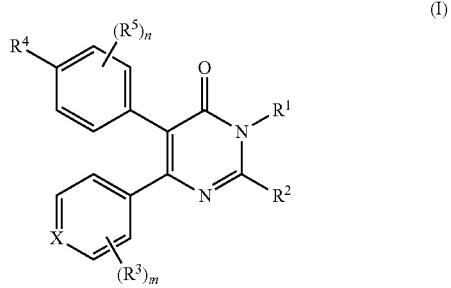

or a pharmaceutically acceptable salt thereof, wherein:
$R^1$ is hydrogen or C1-C6 alkyl;
$R^2$ is C1-C8 alkyl, C1-C8 haloalkyl, C3-C8 cycloalkyl, or —$NR^A R^B$;
$R^A$ and $R^B$ are independently hydrogen or C1-C6 alkyl, or $R^A$ and $R^B$ together with the nitrogen atom to which they are attached form a 4-6 membered heterocyclyl;
each $R^3$ is independently halogen, cyano, hydroxyl, or C1-C6 alkyl;
X is CH, $CR^3$, or N;
$R^4$ is chloro, cyano, hydroxyl, or trifluoromethyl;
each $R^5$ is independently halogen, cyano, hydroxyl, C1-C6 alkyl, or C1-C6 haloalkyl; and
m and n are independently 0, 1, 2, or 3.

2. The compound of Embodiment 1, wherein $R^1$ is C1-C6 alkyl.

3. The compound of Embodiment 1 or 2, wherein $R^1$ is methyl.

4. The compound of Embodiment 1, wherein $R^1$ is hydrogen.

5. The compound of any one of Embodiments 1-4, wherein $R^2$ is C1-C8 alkyl.

6. The compound of any one of Embodiments 1-5, wherein $R^2$ is C3-C5 alkyl.

7. The compound of any one of Embodiments 1-6, wherein $R^2$ is isobutyl.

8. The compound of any one of Embodiments 1-4, wherein $R^2$ is C1-C8 haloalkyl.

9. The compound of any one of Embodiments 1-4, wherein $R^2$ is C3-C8 cycloalkyl.

10. The compound of any one of Embodiments 1-4 or 9, wherein $R^2$ is C3-C5 cycloalkyl.

11. The compound of any one of Embodiments 1-4, wherein $R^2$ is —$NR^A R^B$.

12. The compound of any one of Embodiments 1-4 or 11, wherein $R^A$ is C1-C6 alkyl.

13. The compound of any one of Embodiments 1-4 or 11-12, wherein $R^A$ is methyl.

14. The compound of any one of Embodiments 1-4 or 11, wherein $R^A$ is hydrogen.

15. The compound of any one of Embodiments 1-4 or 11, wherein $R^B$ is C1-C6 alkyl.

16. The compound of any one of Embodiments 1-4, 11, or 15, wherein $R^B$ is methyl.

17. The compound of any one of Embodiments 1-4 or 11, wherein $R^B$ is hydrogen.

18. The compound of any one of Embodiments 1-4 or 11-17, wherein $R^A$ and $R^B$ are the same.

19. The compound of any one of Embodiments 1-4 or 11-17, wherein $R^A$ and $R^B$ are different.

20. The compound of any one of Embodiments 1-4, 11-17, or 19, wherein one of $R^A$ and $R^B$ is hydrogen and the other of $R^A$ and $R^B$ is C1-C6 alkyl.

21. The compound of any one of Embodiments 1-4, 11-17, or 19-20, wherein one of $R^A$ and $R^B$ is hydrogen and the other of $R^A$ and $R^B$ is methyl.

22. The compound of any one of Embodiments 1-4 or 11, wherein $R^A$ and $R^B$ together with the nitrogen atom to which they are attached form a 4-6 membered heterocyclyl.

23. The compound of any one of Embodiments 1-22, wherein m is 1.

24. The compound of any one of Embodiments 1-23, wherein $R^3$ is halogen.

25. The compound of any one of Embodiments 1-24, wherein $R^3$ is chloro.

26. The compound of any one of Embodiments 1-24, wherein $R^3$ is fluoro.

27. The compound of any one of Embodiments 1-23, wherein $R^3$ is cyano.

28. The compound of any one of Embodiments 1-23, wherein $R^3$ is hydroxyl.

29. The compound of any one of Embodiments 1-23, wherein $R^3$ is C1-C6 alkyl.

30. The compound of any one of Embodiments 1-23 or 29, wherein $R^3$ is methyl.

31. The compound of any one of Embodiments 1-30, wherein X is $CR^3$.

32. The compound of any one of Embodiments 1-22, wherein X is CH.

33. The compound of any one of Embodiments 1-22, wherein X is N.

34. The compound of any one of Embodiments 1-22 or 31-33, wherein m is 0.

35. The compound of any one of Embodiments 1-22 or 31-33, wherein m is 2.

36. The compound of any one of Embodiments 1-22 or 31-33, wherein m is 3.

37. The compound of any one of Embodiments 1-36, wherein $R^4$ is chloro.

38. The compound of any one of Embodiments 1-36, wherein $R^4$ is cyano.

39. The compound of any one of Embodiments 1-36, wherein $R^4$ is hydroxyl.

40. The compound of any one of Embodiments 1-36, wherein $R^4$ is trifluoromethyl.

41. The compound of any one of Embodiments 1-40, wherein n is 1.

42. The compound of any one of Embodiments 1-41, wherein $R^5$ is halogen.

43. The compound of any one of Embodiments 1-42, wherein $R^5$ is chloro.

44. The compound of any one of Embodiments 1-42, wherein $R^5$ is fluoro.

45. The compound of any one of Embodiments 1-41, wherein $R^5$ is cyano.

46. The compound of any one of Embodiments 1-41, wherein $R^5$ is hydroxyl.

47. The compound of any one of Embodiments 1-41, wherein $R^5$ is C1-C6 alkyl.

48. The compound of any one of Embodiments 1-41 or 47, wherein $R^5$ is methyl.

49. The compound of any one of Embodiments 1-41, wherein $R^5$ is C1-C6 haloalkyl.

50. The compound of any one of Embodiments 1-41 or 49, wherein $R^5$ is trifluoromethyl.

51. A compound selected from the group consisting of:

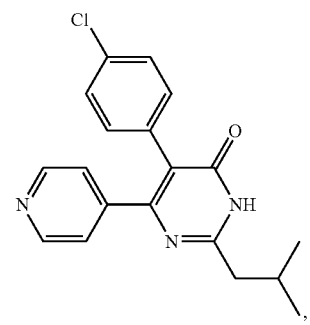

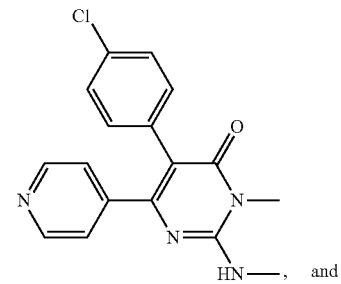, and

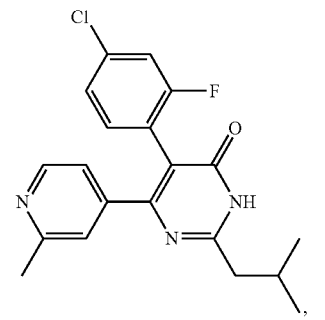, or a pharmaceutically acceptable salt of any of the foregoing.

52. A compound which is 5-(4-chlorophenyl)-2-isobutyl-6-(pyridin-4-yl)pyrimidin-4(3H)-one, or a pharmaceutically acceptable salt thereof, having the structure of

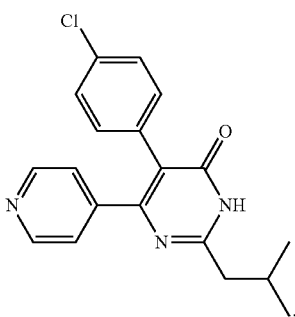

or a pharmaceutically acceptable salt thereof.

53. A compound which is 5-(4-chlorophenyl)-3-methyl-2-(methylamino)-6-(pyridin-4-yl)pyrimidin-4(3H)-one, or a pharmaceutically acceptable salt thereof, having the structure of

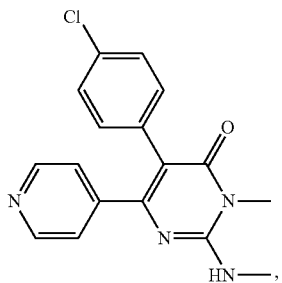 [SMILES: CNc1nc(-c2ccncc2)c(-c2ccc(Cl)cc2)c(=O)n1C]

or a pharmaceutically acceptable salt thereof.

54. A compound which is 5-(4-chloro-2-fluorophenyl)-2-isobutyl-6-(2-methylpyridin-4-yl)pyrimidin-4(3H)-one, or a pharmaceutically acceptable salt thereof, having the structure of

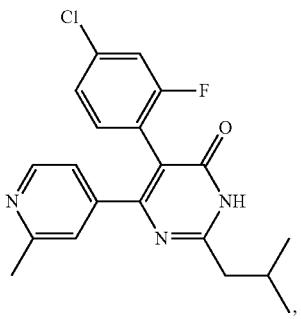 [SMILES: Cc1cc(-c2nc(CC(C)C)[nH]c(=O)c2-c2ccc(Cl)cc2F)ccn1]

or a pharmaceutically acceptable salt thereof.

55. A pharmaceutical composition comprising the compound of any one of Embodiments 1-54, or a pharmaceutically acceptable salt thereof, and one or more pharmaceutically acceptable excipients.

56. A method of treating a CK-1δ-associated neurological disorder in a subject in need thereof, comprising administering to the subject a therapeutically effective amount of a compound of any one of Embodiments 1-54, or a pharmaceutically acceptable salt thereof, or the pharmaceutical composition of Embodiment 55.

57. The method of Embodiment 56, wherein the CK-1δ-associated neurological disorder is amyotrophic lateral sclerosis (ALS), Alzheimer's disease, frontotemporal dementia (FTD), frontotemporal lobar degeneration with ubiquitin inclusions (FTLD-U), or limbic-predominant age-related TDP-43 encephalopathy (LATE).

58. The method of Embodiment 56 or 57, wherein the CK-1δ-associated neurological disorder is ALS.

59. The method of Embodiment 56 or 57, wherein the CK-1δ-associated neurological disorder is Alzheimer's disease.

60. The method of Embodiment 56 or 57, wherein the CK-1δ-associated neurological disorder is FTD.

61. The method of Embodiment 56 or 57, wherein the CK-1δ-associated neurological disorder is FTD-U.

62. The method of Embodiment 56 or 57, wherein the CK-1δ-associated neurological disorder is LATE.

63. A method of inhibiting TDP-43 phosphorylation in a cell comprising TDP-43 and CK-1δ, the method comprising contacting the cell with a compound of any one of Embodiments 1-54, or a pharmaceutically acceptable salt thereof.

OTHER EMBODIMENTS

It is to be understood that while the present disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method of treating ALS in a subject in need thereof, comprising administering to the subject a therapeutically effective amount of a compound which is 5-(4-chlorophenyl)-2-isobutyl-6-(pyridin-4-yl)pyrimidin-4 (3H)-one, or a pharmaceutically acceptable salt thereof, having the structure:

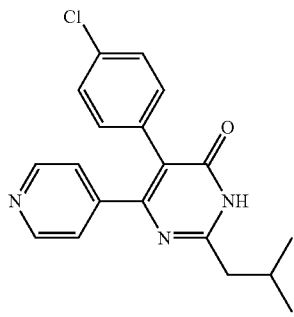 [SMILES: CC(C)Cc1nc(-c2ccncc2)c(-c2ccc(Cl)cc2)c(=O)[nH]1]

or a pharmaceutically acceptable salt thereof.

2. The method of claim 1, wherein the compound is 5-(4-chlorophenyl)-2-isobutyl-6-(pyridin-4-yl)pyrimidin-4 (3H)-one.

3. A method of treating ALS in a subject in need thereof, comprising administering to the subject a therapeutically effective amount of a compound which is 5-(4-chlorophenyl)-3-methyl-2-(methylamino)-6-(pyridin-4-yl)pyrimidin-4 (3H)-one, or a pharmaceutically acceptable salt thereof, having the structure:

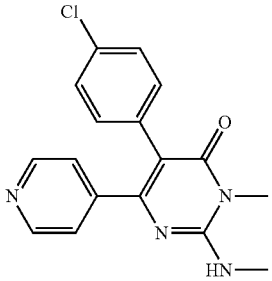 [SMILES: CNc1nc(-c2ccncc2)c(-c2ccc(Cl)cc2)c(=O)n1C]

or a pharmaceutically acceptable salt thereof.

4. The method of claim 3, wherein the compound is 5-(4-chlorophenyl)-3-methyl-2-(methylamino)-6-(pyridin-4-yl)pyrimidin-4 (3H)-one.

5. A method of treating ALS in a subject in need thereof, comprising administering to the subject a therapeutically effective amount of a compound which is 5-(4-chloro-2-fluorophenyl)-2-isobutyl-6-(2-methylpyridin-4-yl)pyrimidin-4 (3H)-one, or a pharmaceutically acceptable salt thereof, having the structure:

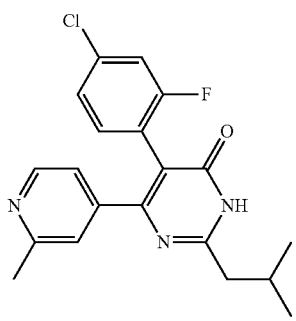 [SMILES: Cc1cc(-c2nc(CC(C)C)[nH]c(=O)c2-c2ccc(Cl)cc2F)ccn1]

or a pharmaceutically acceptable salt thereof.

6. The method of claim 5, wherein the compound is 5-(4-chloro-2-fluorophenyl)-2-isobutyl-6-(2-methylpyridin-4-yl)pyrimidin-4 (3H)-one.

* * * * *